United States Patent
Wu et al.

(10) Patent No.: US 9,138,156 B2
(45) Date of Patent: Sep. 22, 2015

(54) 2D DIPOLE LOCALIZATION USING ABSOLUTE VALUE OF MCG MEASUREMENTS

(75) Inventors: Chenyu Wu, Mountain View, CA (US); Jing Xiao, Cupertino, CA (US)

(73) Assignee: Seiko Epson Corporation, Tokyo (JP)

( * ) Notice: Subject to any disclaimer, the term of this patent is extended or adjusted under 35 U.S.C. 154(b) by 675 days.

(21) Appl. No.: 13/485,172

(22) Filed: May 31, 2012

(65) Prior Publication Data

US 2013/0324832 A1  Dec. 5, 2013

(51) Int. Cl.
*A61B 5/05* (2006.01)
*A61B 5/04* (2006.01)

(52) U.S. Cl.
CPC ......... *A61B 5/04005* (2013.01); *A61B 5/04007* (2013.01); *A61B 5/04008* (2013.01)

(58) Field of Classification Search
USPC ................................................. 600/407–410
See application file for complete search history.

(56) References Cited

U.S. PATENT DOCUMENTS

| | | | |
|---|---|---|---|
| 6,275,719 | B1 | 8/2001 | Kandori et al. |
| 6,463,316 | B1 | 10/2002 | Brungart |
| 7,489,812 | B2 | 2/2009 | Fox et al. |
| 7,668,581 | B2 | 2/2010 | Kandori et al. |
| 2011/0081058 | A1 * | 4/2011 | Wu et al. ........................ 382/128 |

OTHER PUBLICATIONS

Dominguez et al (Enhanced measured synchronization of unchronized sources: inspecting the physiological significance of synchronization analysis of whole brain electrophysiological recordings, International Journal of Physical Sciences vol. 2(11), pp. 305-317, Nov. 2007).*

Haberkorn et al (Pseudo current density maps of electrophysiological heart, nerve or brain function and their physical basis, Biomagnetic research and technology 2006, 4:5).*

Tsukada et al (An iso-integral mapping technique using magnetocardiogram and its possible use for diagnosis of ischemic heart disease, International Journal of Cardiac Imaging 16: 55-666, 2000).*

Dajka, J., et al., "Noisy dynamics of magnetic flux in mesoscopic cylinders", Institute of Physics Publishing, Journal of Physics, Conference Series 30, pp. 321-324, 2006.

Shou, GF., "Towards the Cardiac Equivalent Source Models in Electrocardiogram and Magnetocardiography: A Simulation Study", Computing in Cardiology, Sep. 2010.

Clarke, J., et al., "SQUID—Detected Magnetic Resonance Imaging in Microtesla Fields", Annual Review of Biomedical Engineering, vol. 9, pp. 389-413, Aug. 2007.

* cited by examiner

*Primary Examiner* — Joel F Brutus

(57) ABSTRACT

A magnetic imaging systems produces magnetic magnitude images using magnetic sensors capable of determining only the absolute value of a detected magnetic field and provide no information regarding the positive or negative sign of the detected magnetic image. A 2D dipole location is determines the 2D location of a dipole within a magnetic magnitude image by finding the minimum of the derivative of the absolute value of the magnetic field. This 2D dipole location is then used to determine the 3D position and momentum of a current dipole responsible for the observed magnetic magnitude image. The current dipole is used to generate a magnetic image that incorporate positive and negative sign information.

16 Claims, 14 Drawing Sheets

$$\vec{B}(\vec{r_m}) = \frac{\mu_0}{4\pi} \frac{\vec{J}(\vec{p}) \times (\vec{r_m} - \vec{p})}{\|\vec{r_m} - \vec{p}\|^3}, m = 1 \cdots M \qquad Eq.\ 1$$

$$B_z(\vec{r_m}) = \frac{\mu_0}{4\pi} \frac{[-J^2, J^1] \cdot [r_m^1 - x_p, r_m^2 - y_p]'}{[(r_m^1 - x_p)^2 + (r_m^2 - y_p)^2 + (r_m^3 - z_p)^2]^{3/2}} \qquad Eq.\ 2$$

$$B_z^m(z) = \frac{a_m}{[b_m + (c - z)^2]^{3/2}} \qquad Eq.\ 3$$

$$B_z^m(z + \Delta z) \qquad\qquad Eq.\ 4$$
$$= B_z^m(z) + \frac{d}{dz} B_z^m(z) \cdot \Delta z + \frac{d^2}{2dz} B_z^m(z) \cdot \Delta z^2 + O(\Delta z^3)$$

$$B'_{xy} = \sqrt{\left(\frac{\partial^2 |B_z|}{\partial x^2}\right)^2 + \left(\frac{\partial^2 |B_z|}{\partial y^2}\right)^2} \qquad Eq.\ 5$$

$$\vec{B^m} = \vec{J} \times \vec{R_m} = -\vec{R_m} \times \vec{J} \qquad Eq.\ 6$$

where $\vec{B^m} = \vec{B}(\vec{r_m})$, $\vec{J} = \vec{J}(\vec{p})$ and $\vec{R_m} = \frac{\mu_0}{4\pi} \frac{(\vec{r_m} - \vec{p})}{\|\vec{r_m} - \vec{p}\|^3}$.

FIG. 10A

$$\vec{B^m} = -[\vec{R_m}]_\times \vec{J}$$
$$= -\begin{bmatrix} 0 & -R_m^3 & R_m^2 \\ R_m^3 & 0 & -R_m^1 \\ -R_m^2 & R_m^1 & 0 \end{bmatrix} \cdot \begin{bmatrix} J^1 \\ J^2 \\ J^3 \end{bmatrix} \qquad Eq.\ 7$$

$$B_z^m = [R_m^2, -R_m^1] \cdot [J^1, J^2]' \qquad Eq.\ 8$$

$$\underbrace{\begin{bmatrix} B_z^1 \\ B_z^2 \\ \vdots \\ B_z^M \end{bmatrix}}_{\mathbf{B}} = \underbrace{\begin{bmatrix} R_1^2 & -R_1^1 \\ R_2^2 & -R_2^1 \\ \vdots & \vdots \\ R_M^2 & -R_M^1 \end{bmatrix}}_{\mathbf{R}} \cdot \underbrace{\begin{bmatrix} J^1 \\ J^2 \end{bmatrix}}_{\mathbf{J}} \qquad Eq.\ 9$$

$$\mathbf{J} = (\mathbf{R}^T \mathbf{R})^{-1} \mathbf{R}^T \mathbf{B} \qquad Eq.\ 10$$

$$\vec{B^m} = \frac{\mu_0}{4\pi} \frac{\vec{J} \times ((\vec{r_0} + \vec{\delta_m}) - \vec{p})}{\|(\vec{r_0} + \vec{\delta_m}) - \vec{p}\|^3} = \frac{\mu_0}{4\pi} \frac{\vec{J} \times (\vec{\epsilon_0} + \vec{\delta_m})}{\|\vec{\epsilon_0} + \vec{\delta_m}\|^3} \qquad Eq.\ 11$$

FIG. 10B

$$\alpha \vec{B^m} = \frac{\vec{J} \times \vec{\epsilon_0} + \vec{J} \times \vec{\delta_m}}{\|\vec{\epsilon_0} + \vec{\delta_m}\|^3} \qquad Eq.\ 12$$

$$\alpha B_z^m + \frac{-J^2 x_\epsilon + J^1 y_\epsilon + \tau_m^3}{((x_\epsilon + \delta_m^1)^2 + (y_\epsilon + \delta_m^2)^2 + (z_\epsilon + \delta_m^3)^2)^{3/2}} \qquad Eq.\ 13$$
$$= f^m(x_\epsilon, y_\epsilon, z_\epsilon) = 0$$

$$z = d/\sqrt{2},\ \|\vec{J}\| = \frac{4\pi d^2 B_z^{max}}{0.385 \mu_0} \qquad Eq.\ 14$$

FIG. 10C

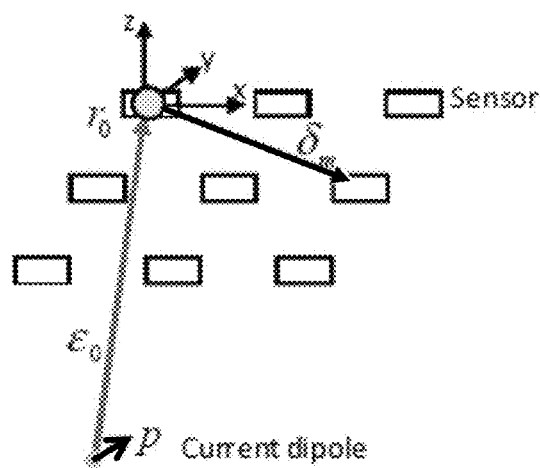

FIG. 16

Error = 5.65669 mm, z = 5cm, No Refine

Error = 8.8091 mm, z = 10cm, No Refine

Error = 7.9196 mm, z = 15cm, No Refine

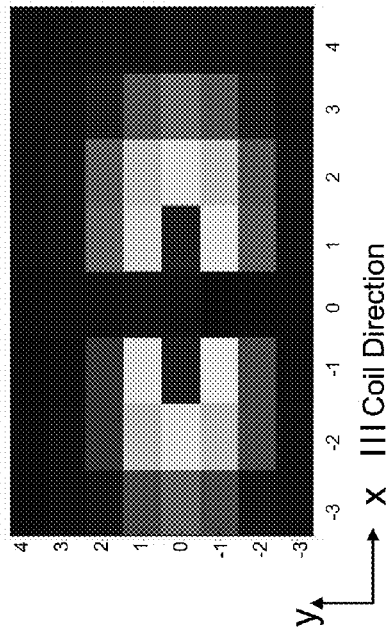
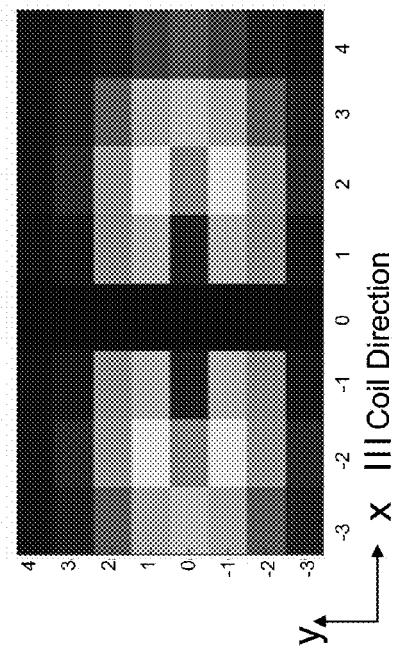
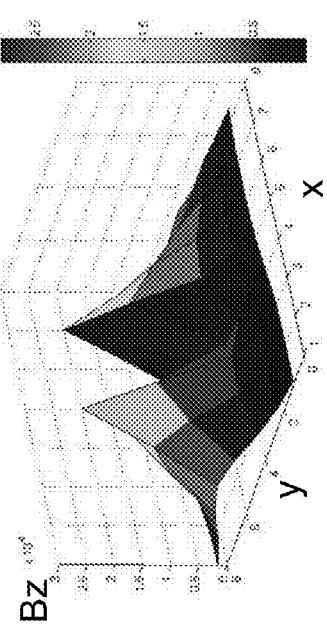
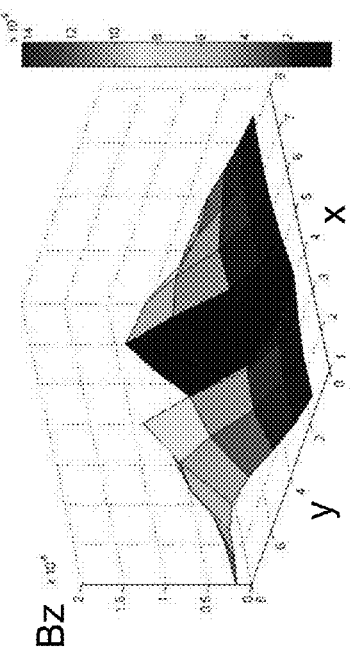
FIG. 17

2D DIPOLE LOCALIZATION USING ABSOLUTE VALUE OF MCG MEASUREMENTS

BACKGROUND

1. Field of Invention

The present invention relates to the field of magnetic imaging. More specifically, it relates to the generating of high quality magnetic imaging using lower quality laboratory equipment that is limited to only measuring the absolute value of an observed magnetic field.

2. Description of Related Art

Electric current source estimation is a common problem in various areas of electromagnetic imaging technology. One area of particular interest is the imaging of electric fields emanating from living tissue. Living organisms generate electric impulses, which result in electric fields, and electric imaging (or electric field imaging) makes it possible to capture images of these electric fields (hereinafter termed electric images). Electric imaging has found wide application in the medical field, where it is often desirable to reconstruct an electric impulse, or dipole, from its electric image.

As it is known in the art, an electric current impulse generates a magnetic field. Thus, organisms that generate electric impulses also generate magnetic fields, and magnetic imaging (or magnetic field imaging) makes it possible to capture images of these magnetic fields (hereinafter termed magnetic images). The study of such magnetic fields in living organisms, or living tissue, is generally known as biomagnetism. Of particular interest in the field of biomagnetism is the magnetic imaging of the human brain and the human heart.

The development of electric imaging and magnetic imaging technology permits the detection and analysis of electrophysiological processes in the brain, heart and other nerve systems. Recording (i.e. imaging) of the electromagnetic fields from such tissues is typically accomplished by placing multiple electric (field) sensors or magnetic (field) sensors around, or over, the tissue being studied. For example, electroencephalography (EEG) uses electric sensors placed around the brain to record electric images of brain tissue, and electrocardiography (ECG or EKG) uses electric sensors placed over the chest to record electric images of heart tissue. Similarly, magnetoencephalography (MEG) uses magnetic sensors placed around the brain to record magnetic images of brain tissue, and magnetocardiography (MCG) uses magnetic sensors placed over the chest to record magnetic images of heart tissue. Examples of an MEG unit and an MCG unit are illustrated in FIGS. 1A and 1B, respectively.

With reference to FIG. 1A, an MEG system consists of a large number (usually 300 or less) of magnetic sensors arranged in a spherical shape (to be fitted around a human head) to provide a high spatial resolution for measurements. The MEG system measures magnetic fields created by brain nerve activity. Each magnetic sensor measures a one-dimensional (1D) magnetic waveform, Bz, in the radial direction.

With reference to FIG. 1B, an MCG system may include a small number (usually 64 or fewer) of magnetic sensors (each sensor is typically a Superconducting Quantum Interference Device, or SQUID) arranged as a sensor planar array. Each SQUID sensor measures a one-dimensional (1D) magnetic waveform (Bz) in the z direction, as illustrated by (x,y,z) axes. The MCG device is usually placed above and within 10 cm of a patient's chest in a location over the patient's heart. Electric current [i.e. electric impulse(s)] in the heart generates a magnetic field B that emanates out from the patient's torso. Each SQUID sensor measure the z-component (i.e. Bz) of the emanating magnetic field B that reaches it. That is, each SQUID sensor measures a 1D magnetic waveform in the z direction, including the positive or negative sign of the magnetic field at the sensor's location.

Compared to electric imaging (or recording) technology such as EEG and ECG, magnetic imaging technology such as MEG and MCG would be preferred due it being more non-invasive and providing a two-dimensional (2D) image (by virtual of the x-y plane of SQUID sensors) at a given point in time. Moreover, the magnetic field generated outside of the human body is not distorted in the direction perpendicular to the body surface (e.g. the radial direction in FIG. 1A and the z-direction in FIG. 1B), due to the magnetic property of body tissue. Thus magnetic imaging has the possibility of being more accurate and sensitive to weak electric activity within the body than is electric imaging.

Magnetic imaging, however, has several limitations. The magnetic fields generated in living tissue are very small. For example, a cerebral magnetic signal is a billion times smaller than the Earth's magnetic field. Consequently, magnetic fields generated in living tissue can easily be obscured by ambient magnetic noise. This can be addressed by using a magnetically-shielded room to reduce background noise. However, one still needs very sensitive magnetic sensors to detect the small magnetic fields emanating from human tissue.

As is explained above in reference to FIG. 1B, an array of SQUIDs are used in the construction of an MCG system. Unfortunately, the size and complexity of SQUIDs limit MCG systems to a relatively small number of SQUID sensors. This limits the resolution of a magnetic image, i.e. an MCG map.

As a result, an MCG system can typically produce only low resolution (low-res) 2D MCG maps. Typically, these low-res 2D MCG maps are not sufficient for diagnosis purposes. For example, a 64 channel Hitachi™ MCG system with a 25 mm sensor interval (as described in "Newly Developed Magneto-cardiographic System for Diagnosing Heart Disease", by Tsukada et al., in Hitachi Review, 50(1):13-17, 2001) only measures an 8×8 MCG map (i.e. it has an 8×8 array of 64 measurement points, or captures). One solution is to increase the number of sensors, but this is very difficult in practice due to the physical size of the sensors and system design constraints.

One approach to overcoming this physical limitation is to approximate a high-resolution (hereinafter, high-res) magnetic image from the low-res image created by the limited number of magnetic sensors. Thus, a necessary step in MCG is generating a high-res, 2D MCG image, or map, from a low-res, 2D MCG image, or map.

Two image examples, L and R, of high-res 2D MCG images generated from low-res images are shown in FIG. 2. Left image L shows the tangential image of a generated high-res MCG image of a healthy heart. The maximal point (i.e. strongest point) within image L indicates the 2D location (or source) of electric current in the heart. Thus, high-res MCG images permits doctors to directly "see" the electrical activity in the heart. Right image R shows the tangential image of a high-res MCG image of an unhealthy heart. It differs significantly from left image L of a healthy heart, and thus provides important cues for diagnosis. Compared to low-res MCG maps, high-res MCG images provide more diagnostic significance.

One way to generate a high-res magnetic field image from a low-res magnetic image is by interpolation. Most modern MCG systems use curve fitting interpolation methods between observed measurements of the electromagnetic sensors to construct high-res 2D MCG images from the low-res 2D MCG maps, such as described in "Magnetocardiographic Localization of Arrhythmia Substrates: A Methodology Study With Accessory Path-Way Ablation as Reference", by B. A. S. et al., in Ann Noninvasive Electrocardiol, 10(2):152-160, 2005, and described in "Evaluation of an Infarction Vector by Magnetocardiogram: Detection of Electromotive Forces that Cannot be Deduced from an Electrocardiogram", by Nomura et al, in Int. Congress Series, 1300:512-515, 2007. Unfortunately, the accuracy of curve fitting methods is typically limited.

As described above, magnetic imaging provides images of the magnetic field at a given time and depth within a tissue. Oftentimes, it would be beneficial to identify the electric current impulse (or current impulse) responsible for the observed magnetic field. Trying to identify the current impulse that generated an observed magnetic image is termed the inverse problem. That is, using the obtained magnetic field measurements at different sites, one attempts to estimate the location and moment of the current source that generated the observed (i.e. the measured) magnetic field.

There are a number of difficulties involved in addressing the inverse problem. According to the Helmholtz reciprocity principal, the inverse problem for MCG is an ill-posed problem unless the prior electric currents and their number are known. For example, a trivia case that assumes a single electric current located at the world origin and far from the sensor array is described in Magnetocardiographic Localization of Arrhythmia Substrates: a Methodology Study with Accessory Pathway Ablation as Reference, Europace, 11(2):169-177, 2009, R. J. et al. This situation cannot be satisfied in practice.

Addressing the inverse problem usually requires that it be simplified by making use of regularization methods (as described in "MEG Inverse Problem with Leadfields", 15th Japan Biomagnetism Conference, 13(1):42-45, 2000, by A. Matani) and that the position of current sources be given a priory (as described in "An Optimal Constrained Linear Inverse Method for Magnetic Source Imaging", Nuclear Science Symposium and Medical Imaging Conference, pages 1241-1245, 1993, by P. Hughett).

Irrespective of the technique used to address the inverse problem, all the techniques make use of captured magnetic images, which provide information of the magnetic flux at a particular point in time at a given depth within a tissue. The capturing of these magnetic images requires specialized, magnetically-shielded rooms and the use expensive MCG equipment comprised of SQUID sensors.

As is explained above, however, SQUID sensors are delicate and complicated devices, and thus not easy to procure for typical laboratory settings. This limits experimental research into the field of magnetic imaging for medical purposes. What is needed is a method of facilitating laboratory experimentation and research in the field of MCG imaging without the use of SQUID sensors.

An object of the present invention is to provide a method of making use of readily available laboratory magnetic sensors to create magnetic images that provide similar information as those provided by MCG images.

Another object of the present invention is to derived positive and negative sign information for a magnetic image from purely magnitude data.

A further object of the present invention is to provide a method of addressing the inverse problem using readily available laboratory magnetic sensors.

A further object of the present invention is to reduce the requirements on laboratory magnetic sensors, by permitting the use of simplified magnetic sensors that only measure the magnitude of a magnetic flux and provide no information regarding its positive or negative sign, i.e. its polarity or direction.

SUMMARY OF INVENTION

The above objects are met in a system/method capable of solving the inverse problem and of generating magnetic images from magnitude images of a magnetic field, or flux. In essence, the present invention simulates MCG medical equipment using readily available laboratory magnetic sensors in an unshielded environment (i.e. a non-magnetically shielded room).

Simulating MCG medical equipment in a laboratory can be difficult and expensive. Most laboratory magnetic field detection equipment, such as the Fluxgate sensor MAG639™, are capable to detecting the magnitude (absolute value) of a magnetic flux (field) at a given point, but cannot determine whether the detected magnetic flux is positive or negative. By contrast, medical MCG equipment requires its magnetic flux detectors to determine not only magnitude, but also its associated positive or negative sign.

The present invention is directed to solving the localization problem (or the inverse problem) using typical laboratory magnetic field detection equipment, which may be used in a phantom setup. More specifically, it provides a method of using readily available, and comparatively inexpensive magnetic flux sensors, such as the Fluxgate sensor MAG639™, that detect only the magnitude of a magnetic flux to generate magnetic images having both positive and negative signs and to localize the current dipole source of the observed magnetic field.

In order to render high resolution MCG images from absolute value data, the present invention makes a single dipole assumption and computes a dense Bxy' (i.e. derivative of Bxy) from a dense |Bz| (utilizing the second derivative of |Bz|) and identifying its minimum.

The above objects are met in a magnetic imaging system, having: magnetic magnitude sensor (MMS) unit providing a first MMS image consisting of an array of capture point data, wherein each capture point datum is the absolute value of a magnetic field in a direction normal to the array at that capture point; a high resolution image synthesizer receiving the first MMS image, the high resolution image synthesizer implementing a linear model of high resolution magnetic magnitude images, the high resolution image synthesizer further projecting the first MMS image into the subspace of the linear model and estimating model coefficients to produce a synthesized second MMS image as a model instance of the linear model, wherein the second MMS image defines a |Bz| map, the |Bz| map being a map of the absolute values of a magnetic field at each data point of the second MMS image in a direction normal to the second MMS image; a two-dimensional (2D) dipole localization unit receiving the second MMS image, the 2D dipole localization unit calculates the derivative of |Bz|, identifies the image minimum of the derivative of |Bz|, and defines the location of the image minimum as the 2D location of a current dipole within the second MMS image.

Preferably, the array of capture point data that make up the first MMS image is an M×M array of capture points; and the magnetic magnitude sensor (MMS) unit has fewer than M×M magnetic sensors, and at least one of the magnetic magnitude sensors takes a separate magnetic magnitude data reading at more than one of the M×M capture point locations to complete the first MMS image.

Alternatively, the array of capture point data that make up the first MMS image is an M×M array of capture points; and the magnetic magnitude sensor (MMS) unit has M×M magnetic sensors, one per capture point in the first MMS image.

Preferably, the array of capture point data that make up the first MMS image is an M×M array of capture points; and the second MMS image has a P×P resolution where P>M.

Additionally, the 2D dipole localization unit defines the 2D location of the dipole within the second MMS as the minimum of the second derivative of |Bz|.

In a preferred embodiment, the linear model is defined by: simulating a plurality of random current impulses within a simulated living tissue, simulating the observed magnetic magnitude image within the living tissue at a plurality of different depth levels within the living tissue as seen from a simulated magnetic magnitude sensor unit of similar resolution as the second MMS image; using the simulated observed magnetic magnitude image as training images in a principle component analysis that defines the linear model.

Additionally, the 2D dipole localization unit calculates the derivative of |Bz| as:

$$B'_{xy} = \sqrt{\left(\frac{\partial^2 |B_z|}{\partial x^2}\right)^2 + \left(\frac{\partial^2 |B_z|}{\partial y^2}\right)^2}$$

The preferred embodiment may further have a three-dimensional (3D) electric current localizer for determining a 3D position and momentum of an electric current in accord with the second MMS image.

In this case, it is preferred that the system also have a magnetic imaging generator receiving position and momentum of the electric current determined by the 3D electric current localizer, and simulating a magnetic image showing positive sign and negative sign magnetic field values. Preferably, the magnetic imaging generator uses the Biot-Savart law to simulate the magnetic image.

Additionally, the 3D electric current localizer may use the 2D location of a dipole within the second MMS image as a starting point in an iterative process for identifying a three-dimensional position vector $\vec{p}$ and momentum vector $\vec{J}$ for the electric current.

The iterative process for identifying position vector $\vec{p}$ and momentum vector $\vec{J}$ for the electric current may include:

(a) defining the Biot-Savart Law as $\vec{B}^m = \vec{J} \times \vec{R}_m = -\vec{R}_m \times \vec{J}$, where $\vec{B}^m = \vec{B}(\vec{r}_m)$, $\vec{J} = \vec{J}(\vec{p})$ and $$\vec{R}_m = \frac{\mu_0}{4\pi} \frac{(\vec{r}_m - \vec{p})}{\|\vec{r}_m - \vec{p}\|^3};$$

(b) expanding this definition of the Biot-Savart Law to a matrix form by using a skew-symmetric matrix:

$$\vec{B}^m = -[\vec{R}_m]_x \vec{J}$$

$$= -\begin{bmatrix} 0 & -R_m^3 & R_m^2 \\ R_m^3 & 0 & -R_m^1 \\ -R_m^2 & R_m^1 & 0 \end{bmatrix} \cdot \begin{bmatrix} J^1 \\ J^2 \\ J^3 \end{bmatrix}$$

where the z component of the magnetic field is computed as:

$$B_z^m = [R_m^2, -R_m^1] \cdot [J^1, J^2]^T$$

where $R_m^1, R_m^2$ are x,y components of $\vec{R}_m$, and for the M×M electromagnetic sensors one has a linear system:

$$\underbrace{\begin{bmatrix} B_z^1 \\ B_z^2 \\ \vdots \\ B_z^M \end{bmatrix}}_{B} = \underbrace{\begin{bmatrix} R_1^2 & -R_1^1 \\ R_2^2 & -R_2^1 \\ \vdots & \vdots \\ R_M^2 & -R_M^1 \end{bmatrix}}_{R} \cdot \underbrace{\begin{bmatrix} J^1 \\ J^2 \end{bmatrix}}_{J}$$

where B is a measured M×1 vector, R is a M×2 position matrix that is computed from given $\vec{p}$ and $\vec{\delta}_m$, and a lease square solution for J provides an estimation of J defined as $J = (R^T R)^{-1} R^T B$;

(c) defining the Biot-Sarvart Law as $$\vec{B}^m = \frac{\mu_0}{4\pi} \frac{\vec{J} \times ((\vec{r}_O + \vec{\delta}_m) - \vec{p})}{\|(\vec{r}_O + \vec{\delta}_m) - \vec{p}\|^3} = \frac{\mu_0}{4\pi} \frac{\vec{J} \times (\vec{\varepsilon}_O + \vec{\delta}_m)}{\|\vec{\varepsilon}_O + \vec{\delta}_m\|^3}$$

letting $\alpha = 4\pi/\mu_0$ and $\vec{\varepsilon}_O = \vec{r}_O - \vec{p}$, identifying $\vec{\delta}_m$ as known for each sensor to redefining the Biot-Sarvart Law as $$\alpha \vec{B}^m = \frac{\vec{J} \times \vec{\varepsilon}_O + \vec{J} \times \vec{\delta}_m}{\|\vec{\varepsilon}_O + \vec{\delta}_m\|^3}$$

letting $\vec{\tau}_m = \vec{J} \times \vec{\delta}_m$ and $\vec{\varepsilon}_O = (x_\epsilon, y_\epsilon, z_\epsilon)^T$ and computing $\vec{\tau}_m$ from $\vec{J}$, for each sensor m=1: M, defining a nonlinear equation in terms of $(x_\epsilon, y_\epsilon, z_\epsilon)$ as $$\alpha B_z^m + \frac{-J^2 x_\epsilon + J^1 y_\epsilon + \tau_m^3}{((x_\epsilon + \delta_m^1)^2 + (y_\epsilon + \delta_m^2)^2 + (z_\epsilon + \delta_m^3)^2)^{3/2}} = f^m(x_\epsilon, y_\epsilon, z_\epsilon) = 0$$

letting $F = (f^1; f^2; \ldots ; f^M) = 0$, and solving a least square solution of the nonlinear system F for $\vec{\varepsilon}_O$;

(d) using $\vec{\varepsilon}_O$ from step (c) to update the position matrix R and recompute J as in step (b), and iteratively repeating steps (b) and (c) until converges is achieved; and (e) defining the $\vec{p} = \vec{r}_O - \vec{\varepsilon}_O$, and defining the initial depth z and magnitude $\|\vec{J}\|$ of the electric current as $$z = d/\sqrt{2} \cdot .3 \text{ cm}, \quad \|\vec{J}\| = \frac{4\pi d^2 B_z^{max}}{0.385 \mu_0}$$

where d is the distance between two magnetic poles in the third MCG image.

The above objects are also met in a magnetic imaging method, having: providing a first magnetic magnitude sensor (MMS) image consisting of an array of capture point data, wherein each capture point datum is the absolute value of a magnetic field in a direction normal to the array at that capture point; inputting the first MMS image to a high resolution image synthesizer, the high resolution image synthesizer implementing a linear model of high resolution magnetic magnitude images, the high resolution image synthesizer further projecting the first MMS image into the subspace of the linear model and estimating model coefficients to produce a synthesized second MMS image as a model instance of the linear model, wherein the second MMS image defines a |Bz| map, the |Bz| map being a map of the absolute values of a magnetic field at each data point of the second MMS image in a direction normal to the second MMS image; inputting the second MMS image to a two-dimensional (2D) dipole localizer, the 2D dipole localizer calculating the derivative of |Bz|, identifying the image minimum of the derivative of |Bz|, and defining the location of the image minimum as the 2D location of a current dipole within the second MMS image.

In this case, the array of capture point data that make up the first MMS image is an M×M array of capture points; and the second MMS image has a P×P resolution where P>M.

Additionally, the 2D dipole localizer unit defines the 2D location of the dipole within the second MMS as the minimum of the second derivative of |Bz|.

Preferably, the linear model is defined by: simulating a plurality of random current impulses within a simulated living tissue, simulating the observed magnetic magnitude image within the living tissue at a plurality of different depth levels within the living tissue as seen from a simulated magnetic magnitude sensor unit of similar resolution as the second MMS image; using the simulated observed magnetic magnitude image as training images in a principle component analysis that defines the linear model.

In an embodiment, the 2D dipole localizer calculates the derivative of |Bz| as:

$$B'_{xy} = \sqrt{\left(\frac{\partial^2 |B_z|}{\partial x^2}\right)^2 + \left(\frac{\partial^2 |B_z|}{\partial y^2}\right)^2}$$

This method may further use a three-dimensional (3D) electric current localizer for determining a 3D position and momentum of an electric current in accord with the second MMS image.

In this case, the method may further have a magnetic imaging generator receiving position and momentum of the electric current determined by the 3D electric current localizer, and simulating a magnetic image showing positive sign and negative sign magnetic field values.

Preferably, the 3D electric current localizer uses the 2D location of a dipole within the second MMS image as a starting point in an iterative process for identifying a three-dimensional position vector $\vec{p}$ and momentum vector $\vec{J}$ for the electric current.

Other objects and attainments together with a fuller understanding of the invention will become apparent and appreciated by referring to the following description and claims taken in conjunction with the accompanying drawings.

BRIEF DESCRIPTION OF THE DRAWINGS

In the drawings wherein like reference symbols refer to like parts.

FIGS. 10A to 10C show various equations (Eq. 1 to Eq. 14) to facilitate discussion of some aspects of the present invention.

versus depth, z.

Figure 13:
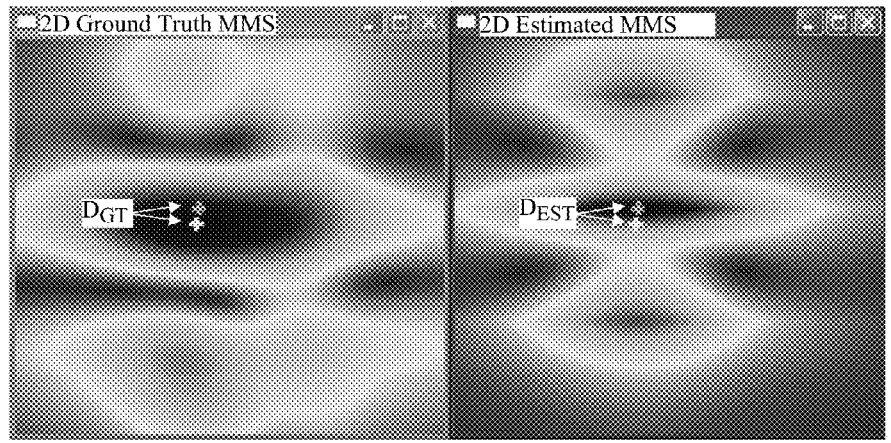
Figure 14:
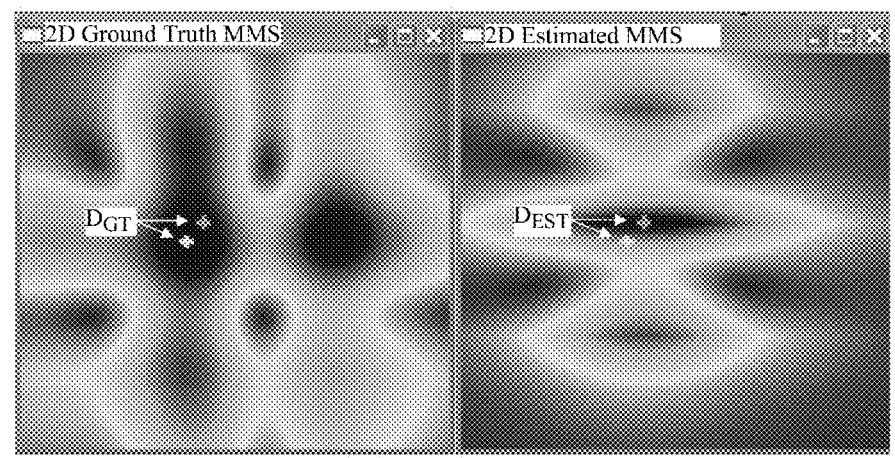
Figure 15:
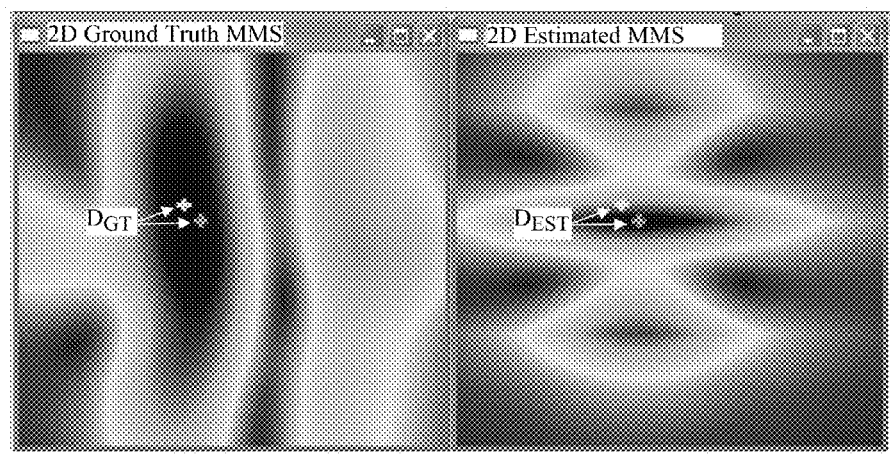

FIGS. 13 to 15 show some examples of the localization error achieved with the present system/method.

FIG. 16 illustrates a setup in the calculation of the inverse problem.

FIG. 17 compares a resultant Bz image with a ground truth Bz image.

Figure 18:
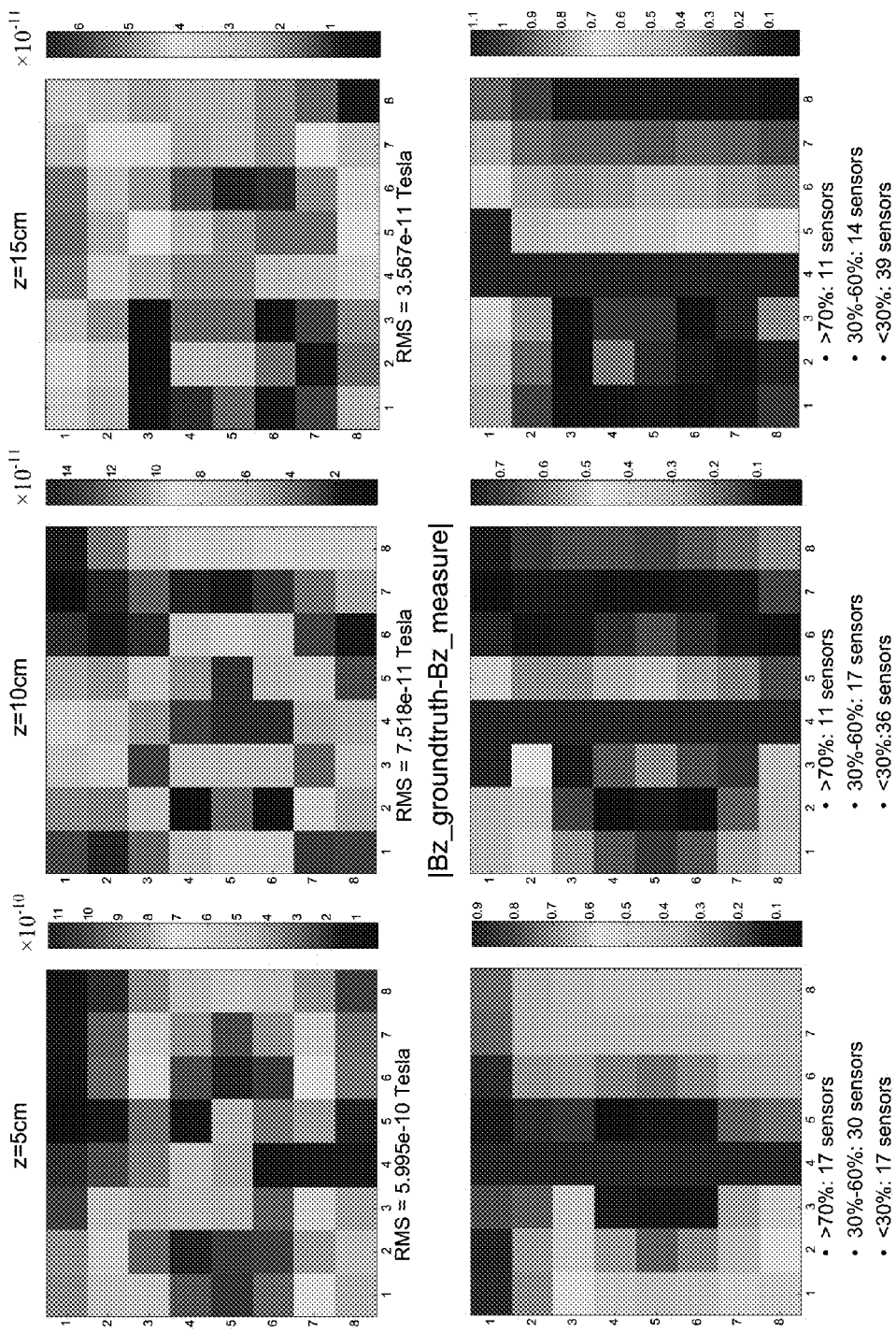

FIG. 18 illustrates the noise levels of some MMS images.

DESCRIPTION OF THE PREFERRED EMBODIMENTS

An MCG system require highly sensitive magnetic sensors to produce images of magnetic fields emanating from living tissue, such as human heart tissue. Due to the high sensitivity requirements of an MCG system, its magnetic sensors are typically comprised of superconducting quantum interference devices (SQUIDs).

Figure 3:
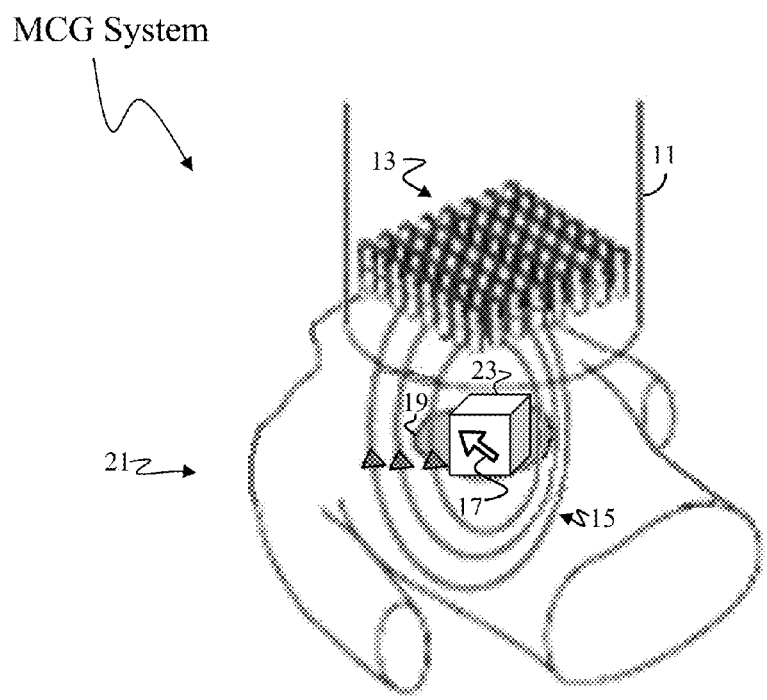
FIG. 3 illustrates an MCG system.

With reference to FIG. 3, a typical MCG system consists of an MCG sensor unit 11 housing a small number of individual SQUID sensors 13 (typically arranged as a planar array of sixty-four or fewer sensors). Electric impulses 17 within the body create a magnetic field 15. In the present case, the human heart 19 functions as the observed source of electric impulses 17 (i.e. as the current source).

Each SQUID sensor 13 is a capture point, and hereinafter may be referred to as a capture 13. Each capture 13 measures a one-dimensional (i.e. 1D) magnetic waveform in a direction perpendicular to the sensor planar array (i.e. the z-direction) emanating from the patient's chest 21 (i.e. human torso). By aligning (or synchronizing) the depth measures (i.e. the 1D magnetic waveform) of the array of captures 13 at a given depth in the z-direction, a two-dimensional (2D) MCG map at the given depth may be constructed. The MCG sensor unit 11 is usually placed five to ten centimeters above the patient's chest 21, and measures the patient's heart magnetic field in a non-invasive manner. Thus, the array of captures 13 measure a collection of low resolution (hereinafter, low-res), two-dimensional (2D) MCG maps of electromagnetic activity.

In order to better interpret the low-res, 2D MCG image maps, it is helpful to make use of a model of electrical activity in the given tissue, i.e. the human heart in the present case. Preferably, this model is a high resolution (herein after high-res) model capable of receiving low-res, 2D MCG maps of electromagnetic activity, and outputting simulated high-res, 2D MCG maps that correspond to the low-res, 2D maps. This may be achieved by simulating heart 19 as a block of heart tissue 23, and defining a high-res model based on block of heart tissue 23.

Although superconducting quantum interference devices (SQUIDs) provide the necessary magnetic sensitivity, they are complicated, expensive and relatively large devices that must be used in highly specialized, magnetically shielded rooms. Part of the difficulty of using SQUIDs is that although they are typically constructed of "high temperature" superconductive material, they still require liquid nitrogen to cool them down enough to achieve superconductivity. The need for liquid nitrogen complicates their design and hinders miniaturization attempts.

Figure 4:
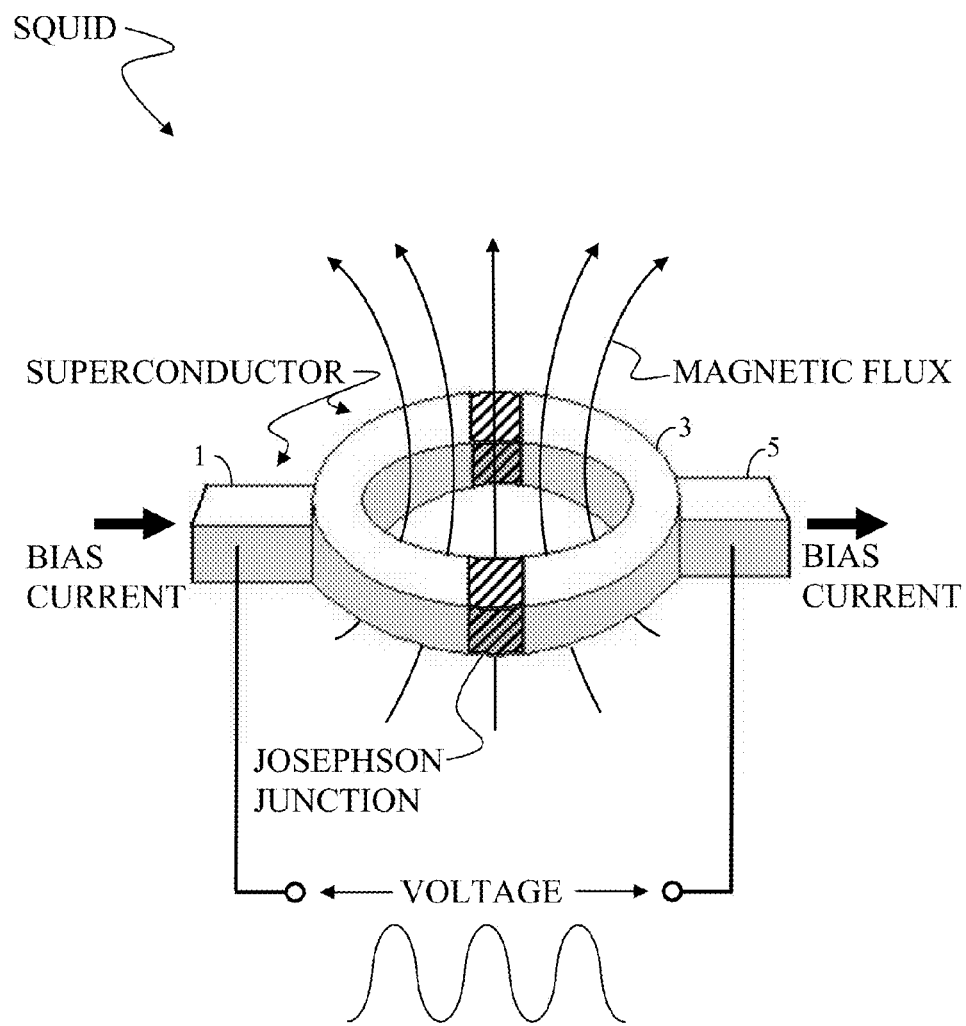
FIG. 4 shows a conceptual illustration of a SQUID.

A conceptual illustration of a SQUID is shown in FIG. 4. A SQUID is a very precise magnetometer for measuring extremely weak magnetic field changes, such as small changes in the human body's electromagnetic field. SQUIDs use a combination of superconducting materials and Josephson junctions to measure magnetic fields as low as $5 \times 1^{-18}$ T. To illustrate, a SQUID can detect a change in energy as much as 100 billion times weaker than the electromagnetic energy that moves a compass needle.

In operation, a bias current enters a first end 1 of the SQUID, is split as it passes through a superconductive ring 3, and is recombined as it exits at a second end 2 on the opposite side. Because of the characteristic of superconductive materials, the bias current establishes a standing wave within the SQUID. This standing wave is split in half along both arms of the superconductive ring 3, and is recombined at its exit end (second end 2, for example). The SQUID uses two Josephson Junctions, each of which is a thin layer of a non-superconductive or a non-conductive material. Because of quantum tunneling, the SQUID is still able to achieve superconductivity, but the Josephson Junctions lower the critical current density of the SQUID, which is the maximum current that the device can carry without dissipation. This stretches the standing wave to the extent that a phase difference can be detected when the standing wave that is split along both arms of ring 3 is recombined at its exit end. A magnetic flux (or magnetic field) that enters perpendicular to conductive ring 3 induces an opposing current in ring 3 resulting in a phase shift difference in the two arms of ring 3 that produces an interference pattern when the standing waves in both arms of ring 3 are recombined. This interference can be constructive interference or destructive interference, and results in a slight voltage fluctuation that can be observed across the first end 1 and the second end 2. Thus, changes in a magnetic field produce phase differences that can be observed as positive and negative fluctuations. This ability of SQUIDs to provide a sign (a positive sign or negative sign) to observed changes in magnetic flux is critical to the interpretation of an MCG system's magnetic image.

Due to the expense and complicated nature of an MCG system, they are not readily available in a typical laboratory setting. This limits research in the field of highly sensitive magnetic images. The need for SQUID sensors also limits the development of less expensive MCG system in particular and magnetic imaging systems in general.

Figures 1A, 1B:
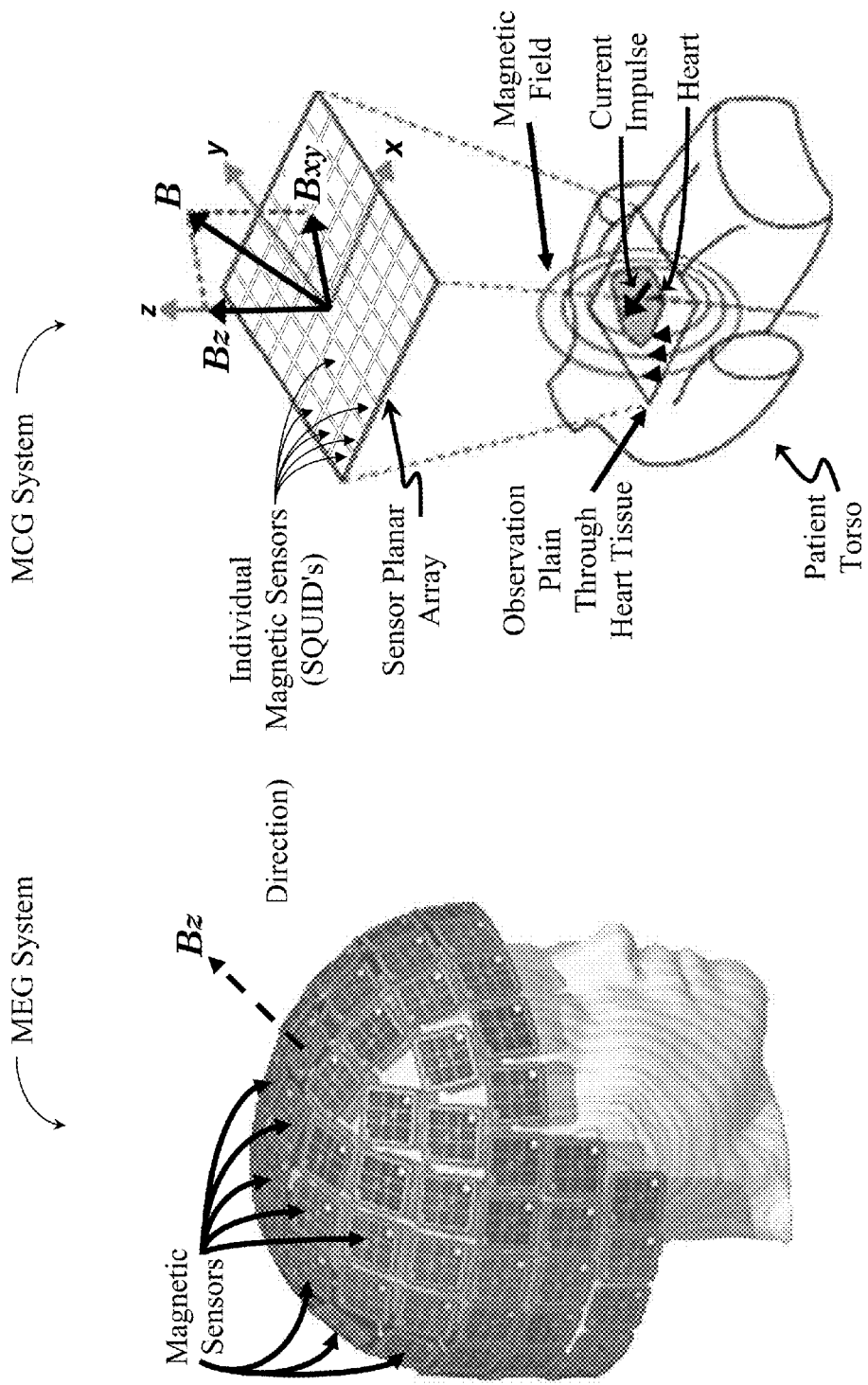
FIGS. 1A and 1B are examples of an MEG unit and an MCG unit, respectively.
Figure 2:
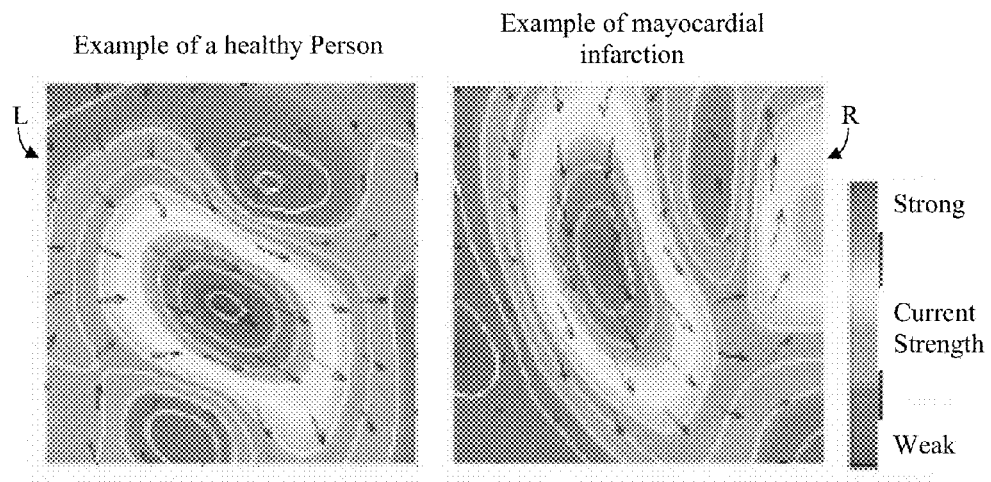
FIG. 2 shows two image examples of high-res 2D MCG images.

A laboratory setting wanting to simulate an MCG image may construct a phantom setup using comparatively simple magnetic sensors capable of observing only the magnitude (i.e. the absolute value) of an observed Bz (the magnetic field in the direction perpendicular to an observation plane) at a given point in time and space, as illustrated in FIGS. 1B and 3. By contrast, standard MCG systems measure the Bz with both positive and negative sign information. Existing methods of interpreting MCG magnetic images, and in particular methods that attempt to localize a magnetic dipole source from a given magnetic image, require this positive and negative sign information. Since most existing phantom setups only provide the amplitude of Bz (i.e. the magnitude of Bz, or |Bz|), the typical localization methods used with MCG images are not applicable to the phantom setting. It will presently be shown how the magnitude-only information provided by the present phantom setting can be used to recover sign information to generate magnetic images having both positive and negative sign information, such as are produced by a typical MCG system.

Figure 5:
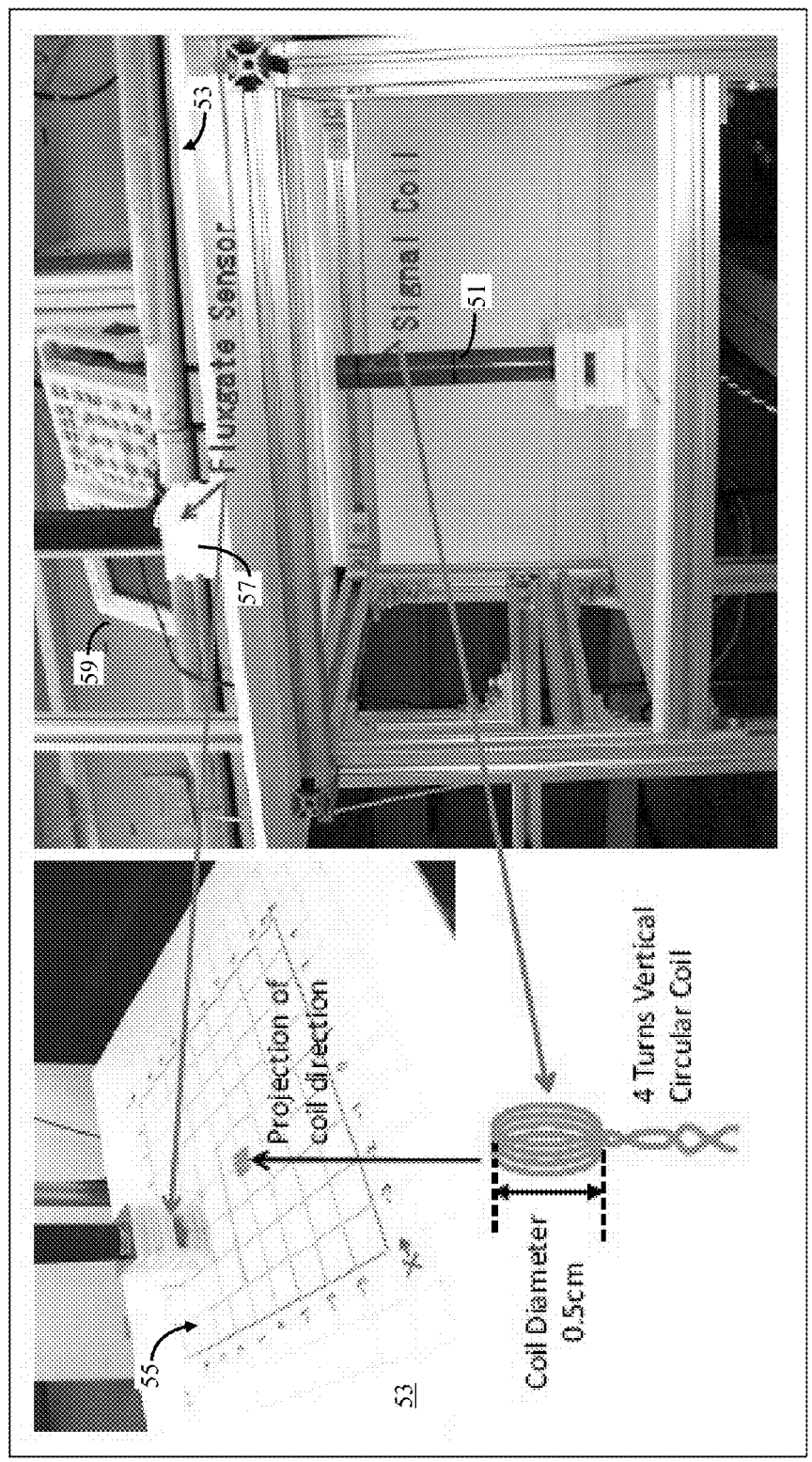
FIG. 5 illustrates a real phantom experiment.

A typical phantom setup in accord with the present invention is illustrated in FIG. 5. In this illustrative setup, a 4-turn vertical circular coil 51 is used as the ground truth current. It is built in a "Signal Coil" component. Above the coil there is a table 53 with a fixed (x,y) position but a varying z position with respect to the coil 51. On the table is printed an 8×8 grid 55 marked in 2 cm intervals, spanning from −4 to +3 in each direction. The coil 51 is right below the (0,0) coordinate. A magnetic magnitude sensor, MMS, (i.e. fluxgate sensor 57, which is preferably a MAG639™ magnetic sensor) is used to measure the absolute value of the z component of the magnetic field at each grid point. In this simplified case, fluxgate sensor 57 may be moved to each grid point to separately measure the absolute value of the z component of the magnetic field at each grid point. A spectrum analyzer 59 is used to read the signal from fluxgate sensor 57.

In this phantom experiment, the electric current (i.e the dipole current source(s) of an observed magnetic field) has a physical shape and size. It can be considered as a set of small line segment currents. The present localization algorithm estimates the 2D position of the geometric center of the coil. By synchronizing the fluxgate sensor measurement with the AC generator, one can simulate an 8×8 MCG system. The output of the fluxgate sensor 57 is imported to the spectrum analyzer 59 and converted to measurements in Tesla.

Alternatively, one could use an array of 8×8 magnetic magnitude sensor (i.e. fluxgate sensors 57) to simulate an 8×8 MCG system. In either case, each fluxgate sensor 57 takes the place of a SQUID 13 and each fluxgate sensor 57 provides capture point, or capture 13, as is explained above in reference to FIG. 3.

Further preferably, the phantom setup of FIG. 5 is unshielded (i.e. not located within a magnetically shielded room) and the measurement noise is thus very high. The present invention therefore provides a very high level of noise rejection in order to provide an accurate localization of a current dipole source of a low-res image (or map) created with the magnetic magnitude sensors.

Before discussing the present invention in detail, it may be helpful to first describe the general flow of a simplified process/system using a magnetic magnitude sensor (MMS) or an plurality/array of MMS's to localize a current source from an observed data map of magnetic field magnitudes.

Figure 6:
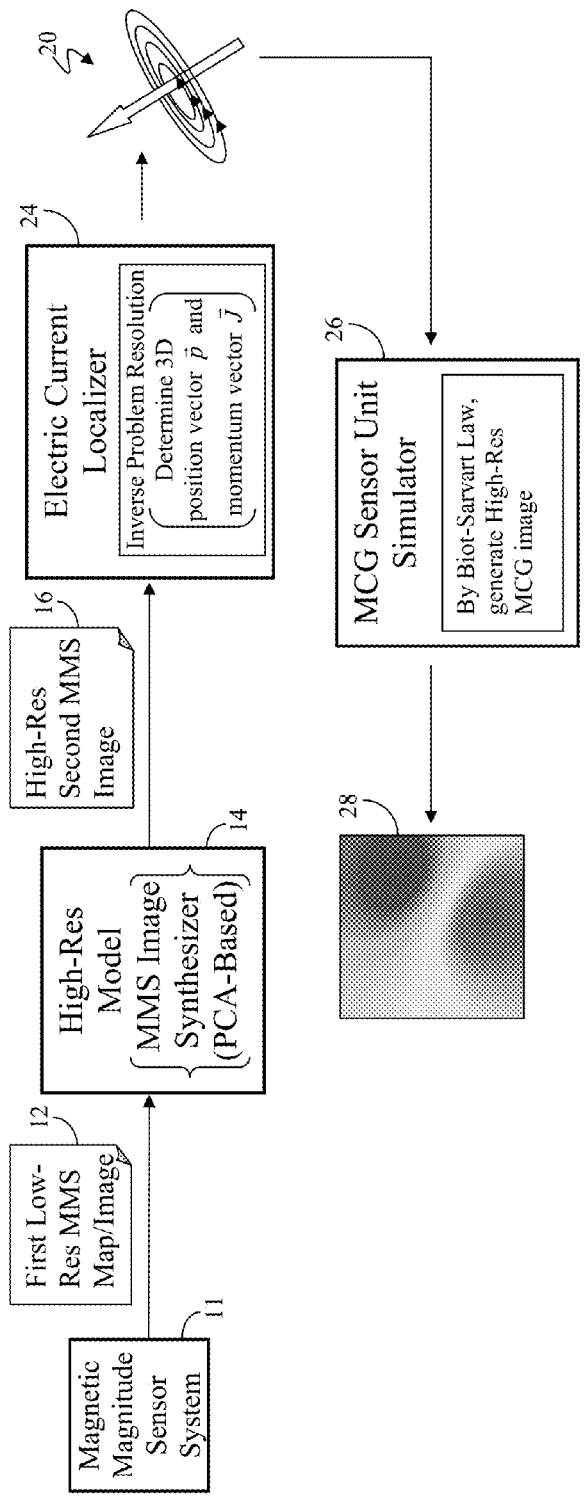
FIG. 6 illustrates a general flow of a simplified process an MMS system/method in accord with the present invention.

With reference to FIG. 6, a system using one or more magnetic magnitude sensor(s) 11 (such as the phantom setup of FIG. 5) produces a first low-res MMS map, or image, 12, as explained above. This first low-res MMS image 12 is than passed to high-res model 14, which produces a high-res, 2D second MMS image 16. Preferably, high-res model 14 is based on a principle component analysis (PCA) of a multitude of training high-res images, as is explained in more detail below.

High-res second MMS image 16 is a higher resolution image representation of first MMS image 12. For example, if first MMS image 12 has an M×M pixel resolution, then second MMS image 16 may have a P×P pixel resolution, where P>>M. Further preferably, second MMS image 16 has a consistent, higher pixel density than first MMS image 12. For example, if first MMS image 12 spans an image area of 20 cm×20 cm, then its pixel density would be M×M pixels per 400 cm², whereas the pixel density for the corresponding, same image area of second MMS image 16 would be P×P pixels per 400 cm². It is noted that if the image area of second MMS image 16 is bigger than that of first MMS image 12, then second MMS image 16 preferably maintains the same pixel density over its entire image area.

Second MMS image 16 is submitted to electric current localizer 24, which resolves the inverse problem to estimate the three-dimensional (3D) location and moment of the current source 20 that as generated magnetic field as depicted in second MMS image 16. It is to be understood that the depiction of MMS image 16 is of the absolute values of the generated magnetic field, and lacks any sign information. Electric current localizer 24 determines the 3D position and momentum of an electric current in accord with the second MMS image 16. Preferably, electric current localizer 24 evaluates electromagnetic output data as they would be observed in individual magnetic sensors of a hypothetical MMS unit in an x-y orientation (Bxy) assuming a single dipole and computes a dense Bxy from a dense Bz, where "B" refers to a magnetic field. Electric current localizer 24 finds minimum of the derivative of Bxy in high-res second MMS image 16, and uses this determined position information as a starting point in an iterative process for identifying a 3D position vector $\vec{p}$ and momentum vector $\vec{J}$ for the electric current 20.

Once 3D position vector $\vec{p}$ and momentum vector $\vec{J}$ of electric current source 20 are known, it is submitted to an MCG sensor unit simulator 26, which generates a final, simulated high-res MCG image 28 by use of the Biot-Savart law. Because the Biot-Savart law includes sign information, MCG image 28 provides sign information as determined from electric current 20.

Thus, the accuracy with which electric current localizer 24 resolves the inverse problem has a direct affect on the accuracy of a desired final objective, or simulation. Before detailing the preferred method/system for resolving the inverse problem, it is beneficial to first describe in more detail a preferred method/system for defining and using high-res model 14.

The present embodiment considers the high-res MMS image restoration (i.e. generation) problem as an exemplar-based super-resolution problem. Typically, exemplar-based problems require a library of true examples (i.e. true sample images) from which to learn characteristics of such true examples. However, since it is impractical to make dense measurements of the magnitudes of dense magnetic fields, it is not feasible to obtain such true examples from directly observed true measurements. Therefore, the presently preferred embodiment uses computer-generated (i.e. synthetic) high-res (training) MMS images as the library of true sample images for training purposes. That is, the present model learning algorithm is based on synthesized high-res MMS images.

The synthesized high-res MMS images that comprise the present library of sample images are preferably randomly generated based on the Biot-Savart Law. From these sample images, a linear model is constructed, preferably by use of principal component analysis (PCA). Sparse, true measurements from a physical system, such as the phantom setup of FIG. 5, may then be projected into the subspace of the thus-constructed linear model to estimate model coefficients and restore (i.e. create, synthesize or generate) a high-res MMS image as a model instance of the linear model. This model instance may be output from the high-res model as a high-res MMS image representation of the low resolution image/map defined by the spare measurements provided by the phantom setup (or other magnetic magnitude sensor system).

Figure 7:
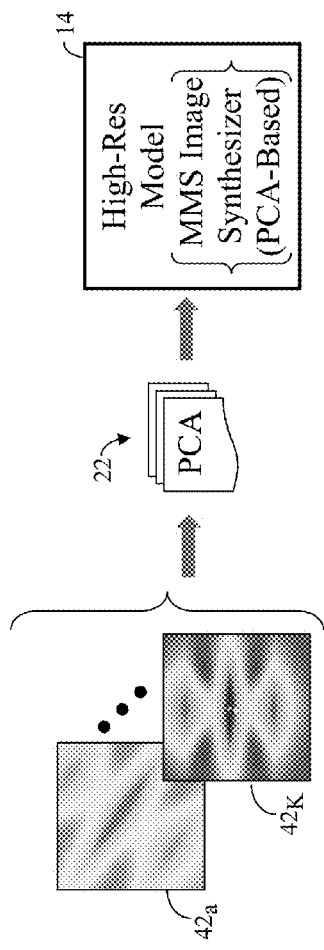
FIG. 7 shows a simplified summary of a preferred method of creating a high-res model by principal component analysis (PCA).

To recapitulate with reference to FIG. 7, a plurality of high-resolution, training images $42_a$ to $42_k$ of the magnitudes of magnetic fields are submitted to a principal component analysis (PCA), block 22, to define high-res model 14. As is explained above, an immediate problem that needs resolving is how to obtain the multitude of high-resolution training images $42_a$-$42_k$. A presently preferred solution to this problem is to simulate the needed, high-resolution training images $42_a$ to $42_k$.

Figure 8:
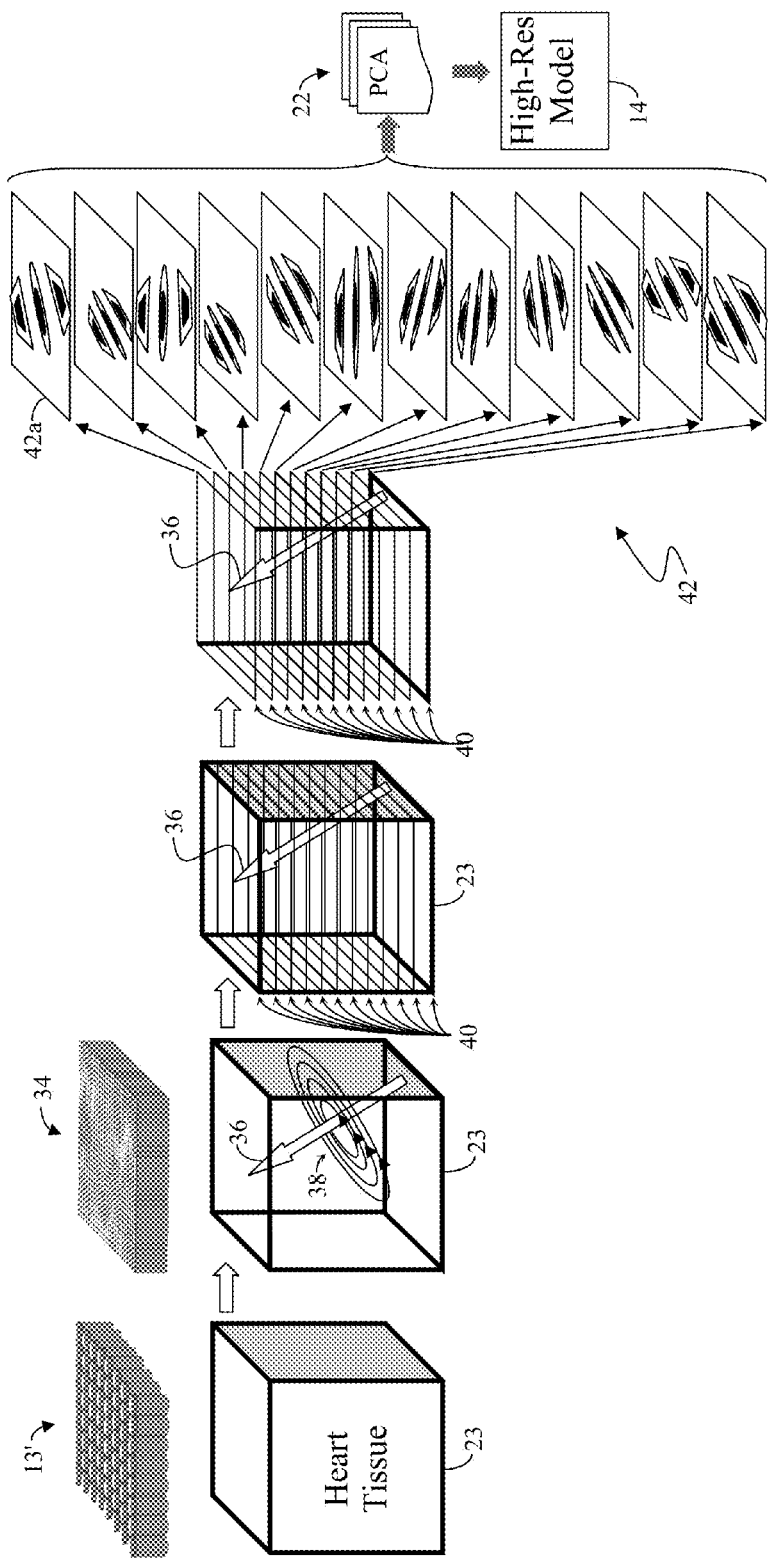
FIG. 8 is a more detailed summary of the system/method of FIG. 7.

With reference to FIG. 8, the basic ideal is to simulate living tissue, such as heart tissue block 23, and then to simulate a plurality of current impulses 36 within heart tissue block 23. Since the physical properties of heart tissue 23 and any other intervening tissues/mediums between heart 19 and physical MMS capture points 13' are known, the propagation of a magnetic field through heart tissue block 23 as generated by current impulses 36 can be simulated. The size of heart tissue block 23 may be of comparable size as heart 19 (or of similar volume as an average human heart). In the present example, MMS capture points 13' may be produced by a single magnetic magnitude sensor unit (i.e. fluxgate sensor 57) that is moved to each of 64 locations to take 64 magnitude measurements, or may be implemented by an 8×8 array of magnetic magnitude sensor units (i.e. a plurality of fluxgate sensors 57).

In FIG. 8, an 8×8 array of magnetic magnitude sensor measurements would provide a low-res data map (i.e. image). To produce high resolution training images, it is preferred that the images be simulated as perceived by a much larger array 34 of magnetic magnitude sensor capture points.

Larger array 34 would provide a similar resolution as the desired high-res training MMS images $42_a$-$42_k$. Random, current impulse 36 could now be defined within heart tissue volume 23, and its resultant magnetic field 38 generated by use of the Biot-Savart Law. Larger array 34 would now make high resolution readings (i.e. generate high-res, training MMS images) of the magnitude of magnetic field 38 at various depths within heart tissue volume 23.

For practical reasons, it is preferred to generate high-res training MMS images at a predefined, limited number of depths, or layers 40 within heart tissue volume 23. The individual layers 40 can then be extracted from heart tissue volume 23, and separated to create individual high-res training MMS images 42 for each depth level. It is to be understood that a multitude of random current impulses would be defined, their magnetic fields generated, and resultant level images created. In one embodiment, 1000 random current impulses are defined, and 1000 sample images are created per depth level. These simulated high-res, training MMS images 42 are then used to construct PCA-based, high-res MMS image model 14.

The present embodiment utilizes various computing devices (or data processing devices) to learn (i.e. create) a linear model from a set of synthesized high-res MMS images generated by random electric impulse currents. Sparse data (i.e. a low resolution image) received from magnetic magnitude sensors are then projected onto the linear model, and a high resolution image representation of the low resolution image is created there from.

Figure 9:
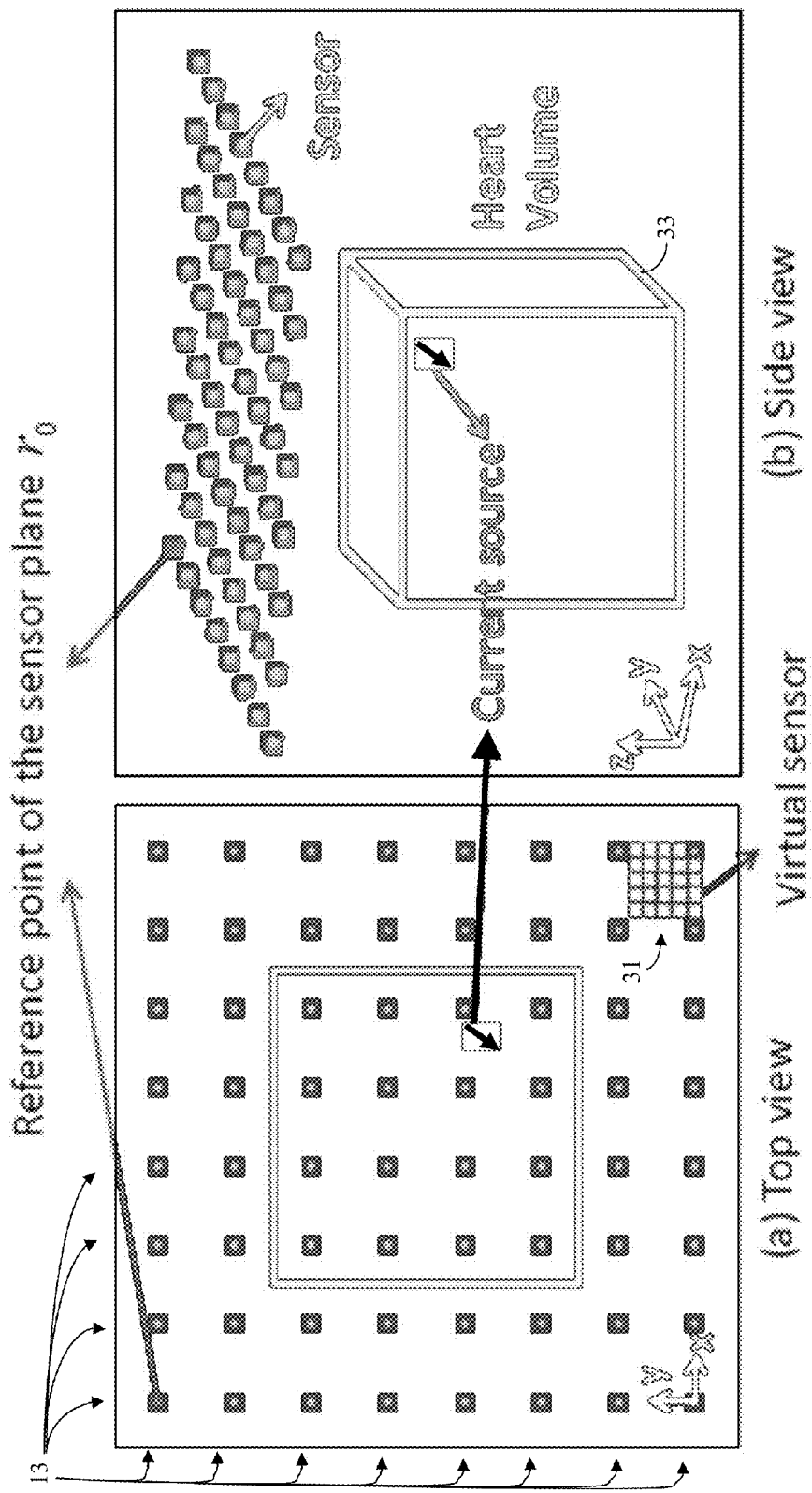
FIG. 9 illustrates the top view and side view of 3D spatial heart volume in a simulation setup.

With reference to FIG. 9, Top View (a) illustrates a top-view of a 2D sensor array (or sensor plane of magnetic magnitude sensors) in relationship to a side-view, 3D spatial heart volume 33 [Side View (b)] in a simulation setup. In the present example, Top View (a) illustrates a top view of an array of 64 magnetic magnitude sensor capture points arranged in an 8×8 sensor array. In the present embodiment, however, a set of four virtual sensor capture points 31 are inserted in-line between adjacent real, physical sensors capture points 13 in the x- and y-directions. Additionally, the square area defined by four corner physical sensor capture points 13 and their four aligned sets of virtual sensor capture points 31 is filled with a 4×4 array of additional virtual sensor capture points 31. Thus, the present embodiment adds 1232 virtual sensor capture points 31 to the 64 physical sensor capture points 13 for a total of 1296 simulated sensor capture points. This is equivalent to a 36×36 sensor array, and constitutes the basis for one implementation of the present, simulated, high-res, training images. Assigning one image pixel per sensor, the present implementation thus provides for P×P (P>8) pixels in a high-res MMS image. Preferably, the sensor plane is 5 cm to 10 cm above heart volume bounding box 33, which in the present case is 10 cm³ (i.e. 10 cm×10 cm×10 cm). In this example, the pixel density in each high-res MMS image would be (1296 pixels)/(100 cm²), or about thirteen pixels per square centimeter (i.e. the high-res image has more than 20 times the resolution of the low-res image). The electric current source is represented by a vector located at a 3D point.

It is to be understood that the number of virtual sensors, and thus the value of P is a design choice. It is also to be understood that since standard MCG devices measure Bz with positive and negative signs, while the presently preferred system (such as the above described phantom setup) measures only the amplitude of Bz (i.e. |Bz|), the interpolation models and localization methods typically used with MCG devices cannot be applied to the present system. A preferred method of constructing a high-res magnetic magnitude image from a low-res magnetic magnitude image, and a preferred method of generating MCG type magnetic images using the present absolute-value-only system are presented below in more detail making use of various equations (Eq. 1 to Eq. 12) shown in FIGS. 10A to 10C.

A first step is to construct a high-res, dense absolute value magnetic image from a low-res, sparse absolute value magnetic image, a second step is then to localize the dipole source of the observed magnetic field, and finally a high-res, dense Bz image similar to those produced by traditional MCG systems is generated.

Given a single electric current, a resultant magnetic field magnitude at each sensor can be computed based on the Biot-Savart Law, equation Eq. 1, where $\vec{J}(\vec{p})$ is the moment of the electric current including its magnitude and orientation. In this case, $\vec{p}$ is the 3-dimensional (i.e. 3D) position vector of the electric current impulse. Note that this representation of electric current impulse is an approximation by assuming the size (or magnitude) of the current is zero. One can consider that the volume (size, or density) information is included in the moment vector $\vec{J}$. $\vec{B}(\vec{r}_m)$ is the magnetic vector measured by the $m_{th}$ sensor at position $\vec{r}_m = \vec{r}_o + \vec{\delta}_m$, where $r_o$ is the reference point of the sensor plane and $\delta m$ indicates the offset of the $m_{th}$ sensor with respect to $r_o$. As it would be understood, $\mu_o$ is the magnetic constant.

The present MMS system measures the magnitude of the z component of $\vec{B}$. Thus, to simulate the present MMS system measurements, one needs to determine the z components of a simulated $\vec{B}$.

From Eq. 1 one may compute $B_z$ (the z component of $\vec{B}$) by means of equation Eq. 2, where $J^1, J^2, J^3$ represent the three components of the current moment vector $\vec{J}$; $x_p, y_p, z_p$ represent the three components of the current position vector $\vec{p}$; and $r_m^1, r_m^2, r_m^3$ represent the three components of the sensor position vector $\vec{r}_m$.

As explained above, a set of high-res P×P MMS images (where P>>M, and P is preferably four times greater than M) are synthesized in a training step. To generate each high-res P×P MMS image, a single electric current with both random moment and random 3D position is defined. The resultant high-res P×P MMS image is computed based on Eq. 2.

Each synthesized high-res MMS image is generated by a single electric current with both random moment and 3D position. Since the magnetic field generated by the heart is very weak ($10^{-12}$ to $10^{-10}$ Tesla), the high-res MMS image is preferably normalized to 0~255 and displayed using a JET color map. In this manner, K high-res MMS training images are generated, i.e. synthesized. All the image vectors are centralized (the mean vector is denoted by $\mu$), and they are stacked into a matrix A. Matrix A thus consists of K columns of P×P vectors. PCA is applied to extract the eigenvectors of matrix A, and thus define an eigenmatrix $\Sigma$.

A received sparse M×M MMS image, as measured by an MMS sensor system, defines a vector g. To restore (i.e. create or define) a high-res MMS image representation of the given sparse M×M measurements (i.e. vector g), one first extracts from the eigenmatrix $\Sigma$ the rows corresponding to the rows defined by the M×M measurements to form a sub-eigenmatrix $\Sigma g$. Similarly, vector g's corresponding elements from mean vector $\mu$ form a sub-mean vector $\mu_g$. Vector g is then projected to sub-eigenmatrix $\Sigma g$, and model coefficients $c_g$ are calculated as $c_g = \Sigma_g^+ (g_j - \mu_g)$, where $\Sigma_g^+$ is the pseudo inverse of $\Sigma g$. Finally the original eigenmatrix $\Sigma$ along with estimated coefficients $c_g$ are used to construct a high-res MMS image vector h, as $h = \Sigma \cdot c_g + \mu$, where h is a P×P vector.

Figure 11:
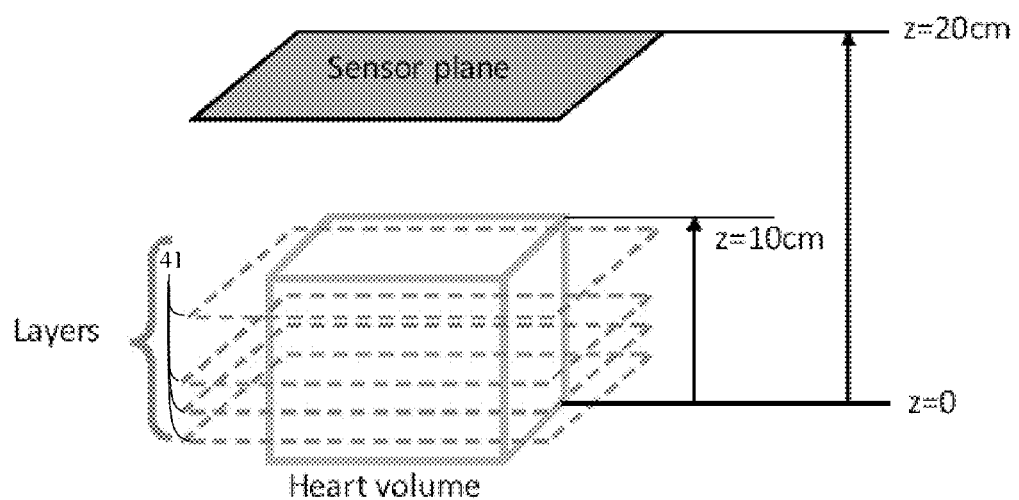
FIG. 11 illustrates depth layers in a heart volume in accord with the present invention.

The synthesized training images are generated for various depth layers. An illustration of some depth layers 41 is shown in FIG. 11. In the presently embodiment, electric current impulses are randomly generated at different depth layers 41. It would be too exhaustive to sample every depth to select a set of depth layers. This approach assumes that $B_z$ can be approximated as a linear function of the current depth.

In the present approach, the sensor positions $\vec{r}_m$, the 2D position $(x_p, y_p)$, and the moment $\vec{J}$ of the electric current are fixed. $B_z$ is only affected by the depth z of the current. Thus, Eq. 2 can be simplified to Eq. 3, where $a_m$ and $b_m$ are constants but unknowns, c=20 cm is the depth of the sensor, and z is the depth of the current, which varies between 0 to 10 cm within the heart volume bounding box. Preferably, $\alpha_m$ lies in a range from −7.5 to 7.5 cm, and $b_m$ lies in a range from 0 to 112.5 cm.

By applying Taylor expansion to Eq. 3, one obtains Eq. 4. By ignoring $O(\Delta z^3)$, one only needs to show that $$\frac{d^2}{2dz} B_z^m(z)$$

is close to zero for any possible z and any sensor.

Figure 12:
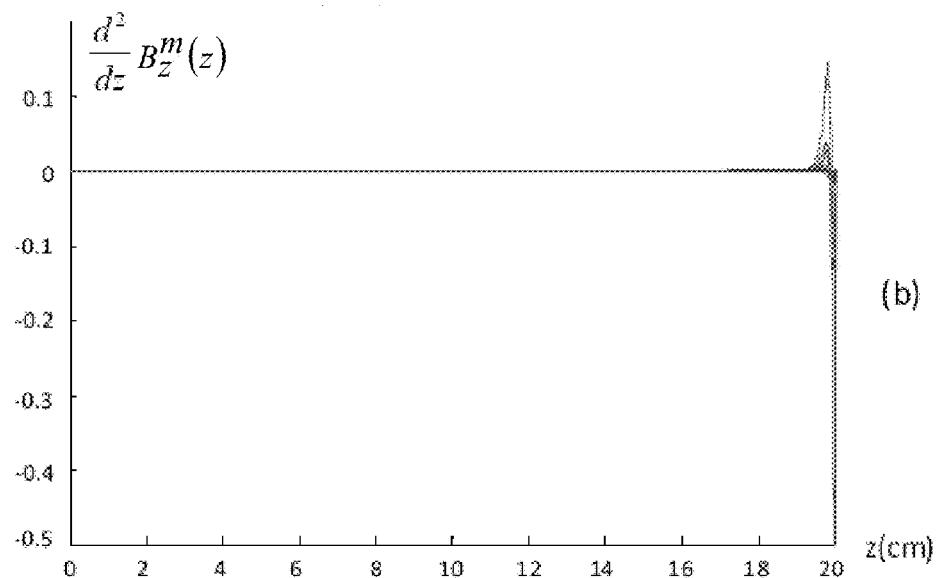
FIG. 12 is a graph of graph of $$\frac{d^2}{2dz} B_z^m(z)$$

A graph of $$\frac{d^2}{2dz}B_z^m(z)$$

versus depth, z, is shown in FIG. 12. More specifically, the graph shows $$\frac{d^2}{2dz}B_z^m(z)$$

in 64 trials with random $\alpha_m$ and $b_m$ in each trial. As shown, $$\frac{d^2}{2dz}B_z^m(z)$$

demonstrates a very small value (close to zero) when z varies from 0 to 10 cm. Therefore, a set of depth layers may be sampled within this depth range, as is illustrated in FIG. 11.

In the present example, one thousand high-res, training MMS image samples were generated in each of 10 evenly distributed depth layers, or levels.

With the high-res, training MMS images thus reconstructed, the generated high-res MMS image may be analyzed to identify the location, depth, magnitude and orientation of an electric current impulse that would produce such an image.

As is explained above, true MMS images obtained from observed physical measurements would typically be comprised of low-res, 2D MMS capture point data maps that do not provide enough information for directly recovering specific electric current impulse information. However, once a high-res MMS image estimation of the low-res, 2D MMS map is constructed, the 2D position of the electric current can be localized from the constructed 2D MMS map. Prior art using traditional MCG images would identify the maximal point of the tangential components of the constructed high-res MCG image as the 2D position of the electric current. Since the present invention uses MMS images, however, this approach does not apply.

A presently preferred method for improving the localization accuracy is to solve a nonlinear optimization that reconstructs both 3D position and moment of the electric current, i.e. the inverse problem. Solving the inverse problem depends on a good initial estimation of the 2D position of the electric current. As is explained below, this 2D position is estimated from the constructed high-res MMS image. The higher the accuracy of the estimated high-res MMS image produced by the linear model, the better the initialization for the inverse problem, which helps it converge on the global optimum more quickly. At the same time, the depth, magnitude and orientation of the electric current are also recovered. More specifically, the present method iteratively alternates between two steps (i.e. alternates between estimating a high-res MMS image using the linear model and resolving the inverse problem from the estimated high-res MMS image). The first step estimates the originating position of 3D electric current impulse, and the second step reconstructs its magnitude and orientation based on the estimated originating position. In the estimating of the originating position of 3D electric current impulse, the 2D current location estimated from the model based restoration is used as the initialization. The present method is efficient, accurate and reliable without the need of special assumptions. For the sake of simplicity, the present system/method is illustrated as applied to a single electric current impulse. It is to be understood, however, that extension of the present system/method/device to multiple current impulses is straightforward.

To estimate the 2D position from a generated high-res MMS image, one first computes a dense first derivative Bxy' from the dense magnetic magnitude |Bz|, as shown in FIG. 5. One then finds the minimum in Bxy', which may be found by taking the derivative of Bxy'. Thus, the present approach uses the second derivative of |Bz| to estimate an initial 2D location for the inverse problem. Using the second derivative of |Bz| may cause the peak to drift, which is a common problem in any filtering based method. This drifting problem can be controlled by an appropriate choice of window size for the filter.

Some examples of the localization error achieved with the present method are shown in FIGS. 13-15. Each of FIGS. 13-15 shows a pair of 2D MMS images at different depths. The image on the left of each pair is a ground truth image, and the image on the right is an estimated MMS image generated using the above-described method. The objective at this stage is to accurate identify the 2D location of the current dipole. The current dipole in the ground truth image is identified as $D_{GT}$ and the estimated 2D current dipole location is identified by $D_{EST}$. FIG. 13 shows that at z=5 cm, the error is 5.6569 mm. At z=10 cm, the error is 8.8091 mm, as shown in FIG. 14, and at z=15, the error is 7.9196 mm.

Having solved the 2D localization problem, the next step is to use it in an iterative process to resolve the inverse problem and find the current impulse responsible for the observed magnetic field.

The inverse problem is to solve both 3D position $\vec{p}$ and moment $\vec{j}$ of the electric current impulse. This approach may be better understood with reference to FIG. 16, where $\vec{r}_o$ is set as the world origin. If $\vec{p}$ is given, the inverse problem becomes a linear one. First, Eq. 1 may be rewritten as Eq. 6, where $\vec{B}^m = \vec{B}(\vec{r}_m)$, $\vec{J} = \vec{J}(\vec{p})$, and $$\vec{R}_m = \frac{\mu_O}{4\pi} \frac{(\vec{r}_m - \vec{p})}{\|\vec{r}_m - \vec{p}\|^3}.$$

Eq. 6 is then expanded to a matrix form by using a skew symmetric matrix, which results in Eq. 7 of FIG. 10B. In this case, the z component of the magnetic field can be computed as shown in Eq. 8, where $R_m^1, R_m^2$ are x,y components of $\vec{R}_m$. Given M sensors, a linear system is defined as illustrated in equation Eq. 9, where B is a measured M×1 vector, R is a M×2 position matrix that is computed from given $\vec{p}$ and $\vec{\delta}_m$. In the present case, J is a 2×1 unknown vector. When rank(R)≥2 (this holds for the single electric current case with 64 sensors), one can solve a least square solution for J, as illustrated in equation Eq. 10.

Note that by only measuring $B_z$ it is impossible to recover $J^3$. In fact, the magnetic field generated by the z component of the current only propagates along the horizontal direction and never reaches outside of the body. For the following computation, one sets $J^3=0$. Given an estimated current moment $\vec{J}=[J,0]$, one can update the current position $\vec{p}$.

Eq. 1 is rewritten as equation Eq. 11. One may then let $\alpha=4\pi/\mu_0$, and $\vec{\epsilon}_0=\vec{r}_0-\vec{p}$. $\vec{\delta}_m$ is known for each sensor. One may then apply equation Eq. 12 to obtain $\alpha \vec{B}^m$. In Eq. 12, let $\vec{\tau}_m = \vec{J} \times \vec{\delta}_m$ and $\vec{\epsilon}_0 = (x_\epsilon, y_\epsilon, z_\epsilon)^T$. It is noted that $\vec{\tau}_m$ can be computed given $\vec{J}$. Again, the cross product is removed from Eq. 12 by using a skew-symmetric matrix. Therefor for each sensor m=1:M, one obtains a nonlinear equation in terms of $(x_\epsilon, y_\epsilon, z_\epsilon)$, as illustrated in Eq. 13. Letting $F=(f^1; f^2; \ldots; f^M)=0$, one then solves a least square solution of the nonlinear system F for $\vec{\epsilon}_0$.

Once the offset $\vec{\epsilon}_0$ is obtained, the position matrix R can be updated and J can be recomputed. These iterations are repeated until the algorithm converges. Finally $\vec{p} = \vec{r}_0 - \vec{\epsilon}_0$. Since the high-res MMS image only provides an estimate for 2D current impulse position $(x_p, y_p)$, the initial depth z and magnitude $\|\vec{J}\|$ of the electric current are given by equation Eq. 14, where d is the distance between two magnetic poles.

With the 3D $\vec{p}$ and momentum vector $\vec{J}$ found, the Biot-Sarvart law may be used to generate a traditional MCG image of Bz with both positive sign and negative sign information (such as via MCG sensor unit simulator 26 of FIG. 6). The resultant Bz images were compared to ground truth Bz image, as illustrated in FIG. 17 and its resilience to noise is illustrated in FIG. 18.

With reference to FIG. 17, the measured (i.e. generated by the present method) Bz plot is shown on the right and the ground truth Bz is shown on the left. As shown, the Bz obtained by the present method is very close to the ground truth.

The top row of images in FIG. 18 show the noise level obtained by taking the difference between the ground truth images and the measured (i.e. generated/estimated) images. The bottom row of images illustrates the percentage error.

As is explained above, the present phantom setup was exposed to a high level of noise. In the present illustration, ¼ of sensors have more than 70% noise, and ½ of sensors have more than 50% noise. In spite of this very high measurement noise, the present method still located all dipoles within an error of not greater than 9 mm. This demonstrates a high level of accuracy.

The 5 mm depth showed the best accuracy, although the RMS error for the measurement was the greatest. This may be because the measurement error closer to the source region is much smaller than the error at 10 mm and 15 mm. The interpolation pattern is closer to the ground truth than the 10 mm and 15 mm cases.

As stated above, using the second derivative of |Bz| may cause the drifting of the peak, but this drifting can be controlled by the window size of the filter.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A magnetic imaging system, comprising:
   magnetic magnitude sensor (MMS) unit that provides a first MMS image that consists of an array of capture point data, wherein each capture point datum is captured as an absolute value of a magnetic field in a direction normal to said array at that capture point;
   a high resolution image synthesizer that receives said first MMS image and projects said first MMS image into a subspace of a linear model of a magnetic magnitude image of higher resolution than said first MMS image and estimates model coefficients to produce a synthesized second MMS image of higher resolution than said first MMS image as a model instance of the linear model, wherein said second MMS image defines a |Bz| map that is a map of absolute values of a magnetic field at each data point of the second MMS image in a direction normal to the second MMS image;
   a two-dimensional (2D) dipole localization unit that receives said second MMS image, calculates a derivative of its defined |Bz| map, identifies a minimum of the calculated derivative of its defined |Bz| map, and designates a location of said minimum as a 2D location of a current dipole within said second MMS image;
   a three-dimensional (3D) electric current localizer that uses said 2D location of the current dipole within said second MMS image as a starting point in an iterative process to identify a 3D position vector $\vec{p}$ and momentum vector $\vec{J}$ for said electric current and;
   a magnetic imaging generator that acquires the 3D position vector $\vec{p}$ and momentum vector $\vec{J}$ of the electric current, and uses them to construct a magnetic image that shows positive sign and negative sign magnetic field values.

2. The magnetic imaging system of claim 1, wherein:
   the array of capture point data that make up said first MMS image is an M×M array of capture points; and
   said magnetic magnitude sensor (MMS) unit has fewer than M×M magnetic magnitude sensors with which to create the M×M array of capture points, and at least one of said magnetic magnitude sensors takes a separate magnetic magnitude data reading at more than one capture point to complete the M×M array of capture points.

3. The magnetic imaging system of claim 1, wherein:
   the array of capture point data that make up said first MMS image is an M×M array of capture points; and
   said magnetic magnitude sensor (MMS) unit has M×M magnetic sensors, one per capture point in said first MMS image.

4. The magnetic imaging system of claim 1, wherein:
   the array of capture point data that make up said first MMS image is an M×M array of capture points; and
   said second MMS image has a P×P resolution where P>M.

5. The magnetic imaging system of claim 1, wherein said 2D dipole localization unit defines the 2D location of the dipole within said second MMS as the minimum of the second derivative of the |Bz| map, said second derivative being the derivative of a first derivative of the |Bz| map.

6. The magnetic imaging system of claim 1, wherein said linear model is defined by:
   simulating a plurality of random current impulses within a simulated living tissue, simulating an observed magnetic magnitude image within the living tissue at a plurality of different depth levels within the living tissue as seen from a simulated magnetic magnitude sensor unit of similar resolution as said second MMS image;
   using the simulated observed magnetic magnitude image as training images in a principle component analysis that defines said linear model.

7. The magnetic imaging system of claim 1, wherein said 2D dipole localization unit calculates the derivative of |Bz| as:

$$B'_{xy} = \sqrt{\left(\frac{\partial^2 |B_z|}{\partial x^2}\right)^2 + \left(\frac{\partial^2 |B_z|}{\partial y^2}\right)^2}.$$

8. The magnitude imaging system of claim 1, wherein said magnetic imaging generator uses the Biot-Savart law to construct said magnetic image.

9. The magnitude imaging system of claim 1, wherein said iterative process to identify position vector $\vec{p}$ and momentum vector $\vec{J}$ for said electric current includes:

(a) defining the Biot-Sarvart Law as $\vec{B}^m = \vec{J} \times \vec{R}_m = -\vec{R}_m \times \vec{J}$, where $\vec{B}^m = \vec{B}(\vec{r}_m)$, $\vec{J} = \vec{J}(\vec{p})$ and $$\vec{R}_m = \frac{\mu_0}{4\pi} \frac{(\vec{r}_m - \vec{p})}{\|\vec{r}_m - \vec{p}\|^3};$$

(b) expanding this definition of the Biot-Sarvart Law to a matrix form by using a skew-symmetric matrix:

$$\vec{B}^m = -[\vec{R}_m]_\times \vec{J}$$
$$= -\begin{bmatrix} 0 & -R_m^3 & R_m^2 \\ R_m^3 & 0 & -R_m^1 \\ -R_m^2 & R_m^1 & 0 \end{bmatrix} \cdot \begin{bmatrix} J^1 \\ J^2 \\ J^3 \end{bmatrix}$$

where the z component of the magnetic field is computed as:

$$B_z^m = [R_m^2, -R_m^1] \cdot [J^1, J^2]^T$$

where $R_m^1, R_m^2$ are x,y components of $\vec{R}_m$, and for said M×M electromagnetic sensors one has a linear system:

$$\underbrace{\begin{bmatrix} B_z^1 \\ B_z^2 \\ \vdots \\ B_z^M \end{bmatrix}}_{B} = \underbrace{\begin{bmatrix} R_1^2 & -R_1^1 \\ R_2^2 & -R_2^1 \\ \vdots & \vdots \\ R_M^2 & -R_M^1 \end{bmatrix}}_{R} \cdot \underbrace{\begin{bmatrix} J^1 \\ J^2 \end{bmatrix}}_{J}$$

where B is a measured M×1 vector, R is a M×2 position matrix that is computed from given $\vec{p}$ and $\vec{\delta}_m$, and a lease square solution for J provides an estimateion of J defined as $J = (R^T R)^{-1} R^T B$;

(c) defining the Biot-Sarvart Law as $$\vec{B}^m = \frac{\mu_0}{4\pi} \frac{\vec{J} \times ((\vec{r}_O + \vec{\delta}_m) - \vec{p})}{\|(\vec{r}_O + \vec{\delta}_m) - \vec{p}\|^3} = \frac{\mu_0}{4\pi} \frac{\vec{J} \times (\vec{\varepsilon}_O + \vec{\delta}_m)}{\|\vec{\varepsilon}_O + \vec{\delta}_m\|^3}$$

letting $\alpha = 4\pi/\mu_0$ and $\vec{\varepsilon}_0 = \vec{r}_0 - \vec{p}$, identifying $\vec{\delta}_m$ as known for each sensor to redefining the Biot-Sarvart Law as $$\alpha \vec{B}^m = \frac{\vec{J} \times \vec{\varepsilon}_O + \vec{J} \times \vec{\delta}_m}{\|\vec{\varepsilon}_O + \vec{\delta}_m\|^3}$$

letting $\vec{\tau}_m = \vec{J} \times \vec{\delta}_m$ and $\vec{\varepsilon}_0 = (x_\epsilon, y_\epsilon, z_\epsilon)^T$ and computing $\vec{\tau}_m$ from $\vec{J}$, for each sensor m=1:M, defining a nonlinear equation in terms of $(x_\epsilon, y_\epsilon, z_\epsilon)$ as $$\alpha B_z^m + \frac{-J^2 x_\varepsilon + J^1 y_\varepsilon + \tau_m^3}{((x_\varepsilon + \delta_m^1)^2 + (y_\varepsilon + \delta_m^2)^2 + (z_\varepsilon + \delta_m^3)^2)^{3/2}} = f^m(x_\varepsilon, y_\varepsilon, z_\varepsilon) = 0$$

letting $F = (f^1; f^2; \ldots; f^M) = 0$, and solving a least square solution of the nonlinear system F for $\vec{\varepsilon}_0$;

(d) using $\vec{\varepsilon}_0$ from step (c) to update the position matrix R and recomputed J as in step (b), and iteratively repeating steps (b) and (c) until converges is achieved; and (e) defining the $\vec{p} = \vec{r}_0 - \vec{\varepsilon}_0$, and defining the initial depth z and magnitude $\|\vec{J}\|$ of the electric current as $$z = d/\sqrt{2.3 \text{ cm}}, \quad \|J\| = \frac{4\pi d^2 B_z^{max}}{0.385 \mu_0}$$

where d is the distance between two magnetic poles in the third MCG image.

10. The magnetic imaging system of claim 1, wherein the magnetic magnitude sensor (MMS) unit captures magnitude-only information.

11. A magnetic imaging method for constructing a magnetic image having positive and negative values from a magnitude magnetic image having only positive values, comprising:

acquiring a first magnetic magnitude sensor (MMS) image provided by a magnetic magnitude sensor unit including a plurality of magnetic magnitude sensors each of which is a separate capture point that provides as capture point data an absolute value measure of an observed magnetic field, said first MMS image consisting of an array of said capture point data, each capture point datum being the absolute value of the observed magnetic field in a direction normal to said array at that capture point, said first MMS image being said magnitude magnetic image;

providing a data processing device to implement the following steps:

inputting said first MMS image to a high resolution image synthesizer, said high resolution image synthesizer implementing a linear model of high resolution magnetic magnitude images, said high resolution image synthesizer further projecting said first MMS image into a subspace of the linear model and estimating model coefficients to produce a synthesized second MMS image of higher resolution than said first MMS image as a model instance of the linear model, wherein said second MMS image defines a |Bz| map, said |Bz| map being a map of the absolute values of a magnetic field at each data point of the second MMS image in a direction normal to the second MMS image;

inputting said second MMS image to a two-dimensional (2D) dipole localizer, said 2D dipole localizer calculating a derivative of the |Bz| map, identifying a minimum of the calculated derivative of the |Bz| map, and designating the location of said minimum as a 2D location of a current dipole within said second MMS image;

inputting the 2D location of the current dipole within the second MMS image to a 3D electric current localizer that uses said 2D location as a starting point in an iterative process to identify a 3D position vector $\vec{p}$ and 3D momentum vector $\vec{J}$ for said electric current;

using a magnetic imaging generator to construct said magnetic image having positive and negative values based on the identified 3D position vector $\vec{p}$ and 3D momentum vector $\vec{J}$.

12. The magnetic imaging method of claim 11, wherein:
the array of capture point data that make up said first MMS image is an M×M array of capture points; and
said second MMS image has a P×P resolution where P>M.

13. The magnetic imaging method of claim 11, wherein said 2D dipole localizer unit defines a 2D location of the dipole within said second MMS as the minimum of a second derivative of the |Bz| map, said second derivative being a derivative of a first derivative of the |Bz| map.

14. The magnetic imaging method of claim 11, wherein said linear model is defined by:
simulating a plurality of random current impulses within a simulated living tissue, simulating a plurality of observed magnetic magnitude images within .the living tissue at a plurality of different depth levels within the living tissue as seen from a simulated magnetic magnitude sensor unit of similar resolution as said second MMS image;
using the plurality of simulated observed magnetic magnitude images as training images in a principle component analysis that defines said linear model.

15. The magnetic imaging method of claim 11, wherein said 2D dipole localizer calculates the derivative of |Bz| as:

$$B'_{xy} = \sqrt{\left(\frac{\partial^2 |B_z|}{\partial x^2}\right)^2 + \left(\frac{\partial^2 |B_z|}{\partial y^2}\right)^2}.$$

16. The magnetic imaging method of claim 11, wherein the magnetic magnitude sensors capture magnitude-only information.

* * * * *